(12) United States Patent
Bieniarz et al.

(10) Patent No.: US 9,310,373 B2
(45) Date of Patent: *Apr. 12, 2016

(54) MOLECULAR CONJUGATE

(71) Applicant: Ventana Medical Systems, Inc., Tucson, AZ (US)

(72) Inventors: Christopher Bieniarz, Tucson, AZ (US); Julia Ashworth-Sharpe, Tucson, AZ (US); Casey A. Kernag, Tucson, AZ (US); Jerome W. Kosmeder, Tucson, AZ (US); Mark Lefever, Oro Valley, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 22 days.

This patent is subject to a terminal disclaimer.

(21) Appl. No.: 14/181,391

(22) Filed: Feb. 14, 2014

(65) Prior Publication Data

US 2014/0205995 A1 Jul. 24, 2014

Related U.S. Application Data

(63) Continuation of application No. 12/687,564, filed on Jan. 14, 2010, now Pat. No. 8,686,122, which is a continuation of application No. 11/603,425, filed on Nov. 21, 2006, now abandoned.

(60) Provisional application No. 60/739,794, filed on Nov. 23, 2005.

(51) Int. Cl.
| | |
|---|---|
| *G01N 33/535* | (2006.01) |
| *G01N 33/58* | (2006.01) |
| *C07C 319/02* | (2006.01) |
| *C07C 323/60* | (2006.01) |
| *C07C 327/28* | (2006.01) |
| *G01N 33/532* | (2006.01) |
| *A61K 47/48* | (2006.01) |
| *A61K 39/44* | (2006.01) |

(52) U.S. Cl.
CPC ............ *G01N 33/581* (2013.01); *C07C 319/02* (2013.01); *C07C 323/60* (2013.01); *C07C 327/28* (2013.01); *G01N 33/532* (2013.01); *A61K 39/44* (2013.01); *A61K 47/4843* (2013.01); *A61K 47/48376* (2013.01); *A61K 47/48384* (2013.01); *G01N 33/535* (2013.01)

(58) Field of Classification Search
CPC .............. A61K 39/44; A61K 47/4843; A61K 47/48376; A61K 47/48384; G01N 33/535
See application file for complete search history.

(56) References Cited

U.S. PATENT DOCUMENTS

| | | |
|---|---|---|
| 3,654,090 A | 4/1972 | Schuurs et al. |
| 3,839,153 A | 10/1974 | Schuurs et al. |
| 4,002,532 A | 1/1977 | Weltman et al. |
| 4,016,043 A | 4/1977 | Schuurs et al. |
| 4,101,380 A | 7/1978 | Rubinstein et al. |
| 4,182,695 A | 1/1980 | Horn et al. |
| 4,200,436 A | 4/1980 | Mochida et al. |
| 4,218,539 A | 8/1980 | Weltman |
| 4,232,119 A | 11/1980 | Carlsson et al. |
| 4,235,960 A | 11/1980 | Sasse et al. |
| 4,433,059 A | 2/1984 | Chang et al. |
| 4,454,226 A | 6/1984 | Ali et al. |
| 4,657,853 A | 4/1987 | Freytag et al. |
| 4,671,958 A | 6/1987 | Rodwell et al. |
| 4,732,863 A | 3/1988 | Tomasi et al. |
| 4,810,638 A | 3/1989 | Albarella et al. |
| 4,994,385 A | 2/1991 | Bieniarz et al. |
| 5,002,883 A | 3/1991 | Bieniarz et al. |
| 5,053,520 A | 10/1991 | Bieniarz et al. |
| 5,057,313 A | 10/1991 | Shih et al. |
| 5,063,109 A | 11/1991 | Bieniarz et al. |
| 5,191,066 A | 3/1993 | Bieniarz et al. |
| 5,648,218 A | 7/1997 | Stults |
| 5,759,808 A | 6/1998 | Casterman et al. |
| 5,789,219 A | 8/1998 | Bieniarz et al. |
| 5,800,988 A | 9/1998 | Casterman et al. |
| 5,840,526 A | 11/1998 | Casterman et al. |
| 5,874,541 A | 2/1999 | Casterman et al. |
| 5,989,842 A | 11/1999 | Schmidt et al. |
| 6,005,079 A | 12/1999 | Casterman et al. |
| 6,015,695 A | 1/2000 | Casterman et al. |
| 6,057,429 A | 5/2000 | Bieniarz et al. |

(Continued)

FOREIGN PATENT DOCUMENTS

| | | |
|---|---|---|
| CN | 1228538 A | 9/1999 |
| CN | 1245561 A | 2/2000 |

(Continued)

OTHER PUBLICATIONS

Bieniarz et al. Extended length heterobifunctional coupling agents for protein conjugates. Bioconjugate Chem. 1996, vol. 7, pp. 88-95.*
Nisnevitch et al. The solid phase in affinity chromatography: strategies for antibody attachment. J. Biochem. Biophys. Methods 2001, vol. 49, pp. 467-480.*
Maassen et al. Synthesis and application of two reagents for the introduction of sulfhydryl groups into proteins. Eur. J. Biochem. 1983, vol. 134, pp. 327-330.*
Akerblom et al., "Preparation and characterization of conjugates of monoclonal antibodies and staphylococcal enterotoxin A using a new hydrophilic cross-linker," *Bioconjugate Chem.* 4(6):455-466, Nov.-Dec. 1993 (Abstract only).
Aldwin et al., "A water-soluble, monitorable peptide and protein crosslinking agent," *Anal. Biochem.* 164(2):494-501, Aug. 1, 1987 (Abstract only).
Anderson et al., "Polymer modification of antibody to eliminate immune complex and Fc binding," *Journal of Immunological Methods*, 109:37-42, 1988.

(Continued)

*Primary Examiner* — Shafiqul Haq
(74) *Attorney, Agent, or Firm* — Charney IP Law LLC; Thomas M. Finetti

(57) ABSTRACT

A method is disclosed for making a conjugate of two molecules using a hydrazide thiol linker. In a particular working embodiment, an Fc-specific antibody-enzyme conjugate is made using the method and demonstrated to provide exceptional staining sensitivity and specificity in immunohistochemical and in situ hybridization assays.

16 Claims, 11 Drawing Sheets
(11 of 11 Drawing Sheet(s) Filed in Color)

(56) References Cited

U.S. PATENT DOCUMENTS

| | | | |
|---|---|---|---|
| 6,124,435 | A | 9/2000 | Ashkenazi et al. |
| 6,160,153 | A | 12/2000 | Bieniarz et al. |
| 6,218,160 | B1 | 4/2001 | Duan |
| 6,252,053 | B1 | 6/2001 | Ohbayashi et al. |
| 6,326,136 | B1 | 12/2001 | Lazar et al. |
| 6,537,519 | B2 | 3/2003 | Borel et al. |
| 6,576,746 | B2 | 6/2003 | McBride et al. |
| 6,613,564 | B2 | 9/2003 | Ohbayashi et al. |
| 6,630,307 | B2 | 10/2003 | Bruchez et al. |
| 6,649,138 | B2 | 11/2003 | Adams et al. |
| 6,670,113 | B2 | 12/2003 | Hainfeld |
| 6,682,596 | B2 | 1/2004 | Zehnder et al. |
| 6,703,196 | B1 | 3/2004 | Klepp et al. |
| 6,800,728 | B2 | 10/2004 | Schwartz |
| 6,815,064 | B2 | 11/2004 | Treadway et al. |
| 2001/0006824 | A1 | 7/2001 | Faatz et al. |
| 2004/0002146 | A1 | 1/2004 | Ohbayashi et al. |
| 2004/0115165 | A1 | 6/2004 | Rosen et al. |
| 2004/0265922 | A1 | 12/2004 | Bieniarz et al. |
| 2005/0012182 | A1 | 1/2005 | Jang et al. |
| 2005/0074499 | A1 | 4/2005 | Tagawa et al. |
| 2005/0100976 | A1 | 5/2005 | Bieniarz et al. |
| 2005/0158770 | A1 | 7/2005 | Bieniarz et al. |
| 2005/0186642 | A1 | 8/2005 | Tacha |
| 2006/0020134 | A1 | 1/2006 | Davis et al. |
| 2006/0246523 | A1 | 11/2006 | Bieniarz et al. |
| 2006/0246524 | A1 | 11/2006 | Bauer et al. |
| 2007/0117153 | A1 | 5/2007 | Bieniarz et al. |
| 2007/0122408 | A1 | 5/2007 | Barbas, III |
| 2009/0181398 | A1 | 7/2009 | Bauer et al. |

FOREIGN PATENT DOCUMENTS

| | | |
|---|---|---|
| CN | 1345417 A | 4/2002 |
| CN | 1345417 A | 4/2002 |
| EP | 0 903 152 | 3/1999 |
| EP | 0 990 903 | 4/2000 |
| EP | 1 118 335 | 7/2001 |
| GB | 782420 | 9/1957 |
| JP | 05-304987 | 11/1993 |
| WO | 85/05638 A1 | 12/1985 |
| WO | WO 85/05638 A1 | 12/1985 |
| WO | WO 90/10621 | 9/1990 |
| WO | WO 92/07268 | 4/1992 |
| WO | 00/52473 A2 | 9/2000 |
| WO | WO 00/52473 | 9/2000 |
| WO | WO 00/54807 | 9/2000 |
| WO | WO 01/12154 | 2/2001 |
| WO | WO 03/031464 | 4/2003 |
| WO | WO 03/072017 | 9/2003 |
| WO | WO 2004/024889 | 3/2004 |
| WO | WO 2004/081053 | 9/2004 |
| WO | WO 2005/001889 | 1/2005 |
| WO | WO 2005/003777 | 1/2005 |
| WO | WO 2006/036646 | 4/2006 |

OTHER PUBLICATIONS

Annuziato et al., "p-maleimidophenyl isocyanate: a novel heterobifunctional linker for hydroxyl or thiol coupling," *Bioconjugate Chem.* 4(3):212-218, May-Jun. 1993 (Abstract only).

Ansell et al., "3-(2-Pyridyldithio)propionic Acid Hydrazide as a Cross-Linker in the Formulation of Liposome-Antibody Conjugates," *Bioconjugate Chem.* 7(4):490-496, 1996.

Arpicco et al., "New coupling reagents for the preparation of disulfide cross-linked conjugates with increased stability," *Bioconjugate Chem.* 8(3):327-337, May-Jun. 1997 (Abstract only).

Atkinson et al., "Potential Antiradiation Drugs. I. Amide, Hydroxamic Acid, and Hydrazine Derivatives of Mercapto Acids. Amino Thioacids," *Journal of Medicinal Chemistry, American Chemical Society* 8:29-33, Jan. 1965.

Bernatowicz et al., "The N-hydroxysuccinimide ester of Boc[S-(3-nitro-2-pyridinesulfenyl)]cysteine: a heterobifunctional cross linking agent," *Biochem. Biophys. Res. Commun.* 132(3):1046-1050, Nov. 15, 1985 (Abstract only).

Bieniarz et al., "Extended Length Heterobifunctional Coupling Agent for Protein Conjugations," *Bioconjugate Chem.* 7(1):88-95, Jan.-Feb. 1996.

Bieniarz et al., "Thermally Stabilized Immunoconjugates: Conjugation of Antibodies to Alkaline Phosphatase Stabilized with Polymeric Cross-Linkers," *Bioconjugate Chem.* 9(3):399-402, Apr. 11, 1998.

Bieniarz et al., "Alkaline phosphatase activatable polymeric cross-linkers and their use in the stabilization of proteins," *Bioconjugate Chem.* 9(3):390-398, May-Jun. 1998 (Abstract only).

Capel et al., "The Effect of 2-Mercaptoethanol on IgM and IgG Antibody Activity," *Journal of Immunological Methods* 36:77-80, 1980.

Carlsson et al., "Protein thiolation and reversible protein-protein conjugation, N Succinimidyl 3-s(pyridyldithio)proprionate, a new heterobifunctional reagent," *Biochem. J.* 173(3):723-737, Sep. 1, 1978 (Abstract only).

Carroll et al., "Enhanced stability in vitro and in vivo of immunoconjugates prepared with 5-methyl-2-iminothiolane," *Bioconjugate Chem.* 5(3):248-256, May-Jun. 1994 (Abstract only).

Chamow et al., "Conjugation of Soluble CD4 without Loss of Biological Activity via a Novel Carbohydrate-directed Cross-linking Reagent," *The Journal of Biological Chemistry* 267(22):15916-15922, 1992.

Chan et al., "Quantum Dot Bioconjugates for Ultrasensitive Nonisotopic Detection," *Science* 281:2016-2018, Sep. 25, 1998.

Chen et al., "The use of bifunctional polyethyleneglycol derivatives for coupling of proteins to and cross-linking of collagen matrices," *J. Mater Sci. Mater Med.*, 13(11):1029-1035, Nov. 2002 (Abstract only).

Chong et al., "A new heterobifunctional cross-linking reagent for the study of biological interactions between proteins. 1. Design, synthesis, and characterization," *J. Biol. Chem.* 256(10):5064-5070, May 25, 1981 (Abstract only).

Collioud et al., "Oriented and covalent immobilization of target molecules to solid supports: synthesis and application of a light-activatable and thiol-reactive cross-linking reagent," *Bioconjugate Chem.* 4(6):528-536, Nov.-Dec. 1993 (Abstract only).

Cunningham-Rundles et al., "Biological activities of polyethyleneglycol immunoglobulin conjugates. Resistance to enzymatic degradation," *Journal of Immunological Methods*,152:177-190, 1992.

del Rosario et al., "Sulfhydryl Site-Specific Cross-Linking and Labeling of Monoclonal Antibodies by a Fluorescent Equilibrium Transfer Alkylation Cross-Link Reagent," *Bioconjugate Chem.* 1(1):51-59, Jan.-Feb. 1990.

Dhawan, "Design and construction of novel molecular conjugates for signal amplification (1): conjugation of multiple horseradish peroxidase molecules to immunoglobulin via primary amines on lysine peptide chains," *Peptides* 23(12):2091-2098, Dec. 2002.

Duncan et al., "A new reagent which may be used to introduce sulfhydryl groups into proteins, and its use in the preparation of conjugates for immunoassay," *Anal. Biochem.* 132(1):68-73, Jul. 1, 1983 (Abstract only).

First Office Action, dated Jun. 4, 2012, issued in related Canada Application No. 2,609,702.

Fischer-Durand et al., "Synthesis of Metal-Carbonyl-Dendrimer-Antibody Immunoconjugates: Towards a New Format for Carbonyl Metallo Immunoassay," *ChemBioChem*, 5:519-525, 2004.

Frisch et al., "Synthesis of short polyoxyethylene-based heterobifunctional crosslinking reagents. Application to the coupling of peptides to liposomes," *Bioconjugate Chem.* 7(2):180-186, Mar.-Apr. 1996 (Abstract only).

Fu et al., "Carbohydrate-directed conjugation of cobra venom factor to antibody by selective derivatization of the terminal galactose residues," *Bioconjugate Chem.* 12(2):271-279, Mar.-Apr. 2001 (Abstract only).

Heindel et al., "A Novel Heterobifunctional Linker for Formyl to Thiol Coupling," *Bioconjugate Chem.* 2(6):427-430, Nov.-Dec. 1991.

Hermanson, *Bioconjugate Techniques*, Academic Press, pp. 71-76, 1996.

(56) References Cited

OTHER PUBLICATIONS

Hinman et al., "Preparation and Characterization of Monoclonal Antibody Conjugates of the Calicheamicins: A Novel and Potent Family of Antitumor Antibiotics," *Cancer Research* 53:3336-3342, Jul. 15, 1993.

Husain et al., "Fc Site-Specific Labeling of Immunoglobulins with Calf Intestinal Alkaline Phosphatase," *Bioconjugate Chem.* 5(5):482-490, Sep.-Oct. 1994.

Huwyler et al., "Receptor Mediated Delivery of Daunomycin Using Immunoliposomes: Pharmacokinetics and Tissue Distribution in the Rat," *J. Pharmacol Exp Ther*, vol. 282(3):1541-1546, 1997.

International Search Report from International Publication No. WO 2007/062177 dated Apr. 1, 2009.

Jeanson et al., "Preparation of reproducible alkaline phosphatase-antibody conjugates for enzyme immunoassay using a heterobifunctional linking agent," *Anal. Biochem.* 172(2):392-396, Aug. 1, 1988 (Abstract only).

Jou et al., "Monoclonal antibodies and a heterobifunctional reagent: a novel approach to the vectorial labeling of selected membrane proteins," *Immunol. Commun.* 11(5):357-375, 1982 (Abstract only).

Kaiser et al., "Basic studies on heterobifunctional biotin-PEG conjugates with 3-(4-pyridyldithio)propionyl marker on the second terminus," *Bioconjugate Chem.* 8(4):545-551, Jul.-Aug. 1997 (Abstract only).

Kortt et al., "Dimeric and trimeric antibodies: high avidity scFvs for cancer targeting," *Biomol. Eng.* 18(3):95-108, Oct. 15, 2001 (Abstract only).

Kossaczka et al., "Synthesis and Immunological Properties of Vi and Di-O-Acetyl Pectin Protein Conjugates with Adipic Acid Dihydrazide as the Linker," *Infection and Immunity* 65(6):2088-2093, Jun. 1997.

Lee et al., "Efficient coupling of glycopeptides to proteins with a heterobifunctional reagent," *Biochemistry* 28(4):1856-1861, Feb. 21, 1989 (Abstract only).

Liberatore et al., "Heterobifunctional cross-linking of a monoclonal antibody with 2-methyl-N1-benzenesulfonyl-N4-bromoacetylquinonediimide," *Biochem. Biophys. Res. Commun.* 158(3):640-645, Feb. 15, 1989 (Abstract only).

Liberatore et al., "Site-directed chemical modification and cross-linking of a monoclonal antibody using equilibrium transfer alkylating cross-link reagents," *Bioconjugate Chem.* 1(1):36-50, Jan.-Feb. 1990 (Abstract only).

Liu et al., "Synthesis, Stability and Cellular Internalization of Gold Nanoparticles Containing Mixed Peptide-Poly(ethylene glycol) Monolayers," *Anal. Chem.* 79:2221-2229, 2007.

Maassen et al., "Synthesis and Application of Two Reagents for the Introduction of Sulfhydryl Groups into Proteins," *Eur. J. Biochem.* 134:327-330, 1983.

Matsuya et al., "A core-shell type fluorescent nanosphere processing reactive pol (ethylene glycol) tethered chains on the surface for zeptomole detection of protein in time-resolved fluorometric immunoassay," *Anal. Chem.* 75(22) 18 pp., Nov. 15, 2003.

Mendintz et al., "Quantum dot bioconjugates for imaging, labeling and sensing," *Nature Materials* 4:435-446, Jun. 2005.

Nisnevitch et al., "The solid phase in affinity chromatography: strategies for antibody attachment," *J. Biochem. Biophys. Methods* 49:467-480, 2001.

Notice of Reasons for Rejection dated Feb. 7, 2012, from Japanese Application No. JP 2008-542455.

Office action issued May 6, 2010, by the European Patent Office for related European Application No. 06838327.2, filed Nov. 21, 2006, 8pp.

Office action issued Oct. 26, 2010, by the European Patent Office for related European patent application No. 06758689.1, filed Apr. 27, 2006, 12 pp.

Office action dated Jun. 30, 2011, U.S. Appl. No. 12/381,638, filed Mar. 13, 2009, 29pp.

Office action issued Jul. 20, 2011, by the Chinese Patent Office for related Chinese Application No. 200680043958.2, filed Nov. 21, 2006, 11pp. (English translation).

Office action issued Apr. 5, 2011, by the Australian Patent Office for related Australian Application No. 2006318438, filed Nov. 21, 2006, 2pp.

O'Shannessy et al., "Specific Conjugation Reactions of Oligosaccharide Moieties of Immunoglobulins," *Journal of Applied Biochemistry* 7(4-5):347-355, 1985.

O'Shannessy et al., "Labeling of the oligosaccharide moieties of immunoglobulins," *Journal of Immunological Methods* 99(2):153-161, May 20, 1987.

O'Sullivan et al., "Enzyme Immunoassay: A Review," *Annals of Clinical Biochemistry* 16:221-240, 1979.

Park et al., "Immunoliposomes Sandwich Fluorometric Assay (ILSF) for Detection of *Escherichia coli* O157:H7," *Journal of Food Science* 69(6): 6 pp., Jul. 27, 2004.

Pasut et al., "Protein, peptide and non-peptide drug PEGylation for therapeutic application," *Expert Opinion on Therapeutic Patents*, 14(6):859-894, 2004.

Peeters et al, "Comparison of four bifunctional reagents for coupling peptides to proteins and the effect of the three moieties on the immunogenicity of the conjugates," *Journal of Immunological Methods* 120(1):133-143, 7989.

*Quanta Biodesign* Catalog, 31 pages, Nov. 5, 2004.

Roberts et al., "Chemistry for peptide and protein PEGylation," *Advanced Drug Delivery Reviews* 54(4):459-476, 2002.

Second Notice of Reasons for Rejection, dated Jun. 19, 2012, issued in corresponding Japanese Patent Application No. 2008-542455.

Second Notice of Reasons for Rejection, dated Jun. 5, 2012, issued in related Japanese Patent Application No. 2008-509141.

Shafer et al., "Activation of Soluble Polysaccharides with 1-Cyano-4- Dimethylaminopyridinium Tetrafluoroborate (CDAP) for use in Protein-Polysaccharide Conjugate Vaccines and Immunological Reagents. II. Selective Crosslinking of Proteins to CDAP-Activated Polysaccharides," *Vaccine* 18:1273-1281, 2000.

Simons et al., "Novel cross-linked enzyme-antibody conjugates for Western blot and ELISA," *Journal of Immunological Methods* 315:88-98, 2006.

Taylor et al., "A Thiolation Reagent for Cell Surface Carbohydrate," *Biochemistry International* 1(4):353-358, Oct. 21, 1980.

Uyeda et al., "Design of Water-Soluble Quantum Dots with Novel Surface Ligands for Biological Applications," *Mat. Res. Soc. Symp. Proc.*, vol. 789, 6 pages, 2004.

Veronese, "Peptide and protein PEGylation: a review of problems and solutions," *Biomaterials* 22:405-417, 2001.

Vogel et al., "Preparation of immunoconjugates using antibody oligosaccharide moieties,"*Methods Mol. Biol.* 283(1):87-108, 2004 (Abstract only).

Wilchek et al., "Labeling Glycoconjugates with Hydrazide Reagents," *Methods in Enzymology* 138:429-442, 1987.

Yan et al., "N-hydroxysuccinimide ester functionalized perfluorophenyl azides as novel photoactive heterobifunctional cross-linking reagents. The covalent immobilization of biomolecules to polymer surfaces," *Bioconjugate Chem.* 5(2):151-157, Mar.-Apr. 1994 (Abstract only).

Zalipsky et al., "Evaluation of a new reagent for covalent attachment of polyethylene glycol to proteins," *Biotechnol. Appl. Biochem.* 15(1):100-114, Feb. 1992 (Abstract only).

Zara et al., "A Carbohydrate-Directed Heterobifunctional Cross-Linking Reagent for the Synthesis of Immunoconjugates," *Anal. Biochemistry* 194:156-162, 1991.

First Office Action, dated Jul. 3, 2015, issued in related China Patent Application No. 201410234039.X.

\* cited by examiner

MOLECULAR CONJUGATE

RELATED APPLICATION DATA

This patent application is a continuation of U.S. patent application Ser. No. 12/687,564, filed on Jan. 14, 2010, now U.S. Pat. No. 8,686,122, which is a continuation of U.S. patent application Ser. No. 11/603,425, filed on Nov. 21, 2006, now abandoned, which claims the benefit of U.S. Provisional Patent Application No. 60/739,794, filed Nov. 23, 2005, all of which are incorporated herein by reference.

FIELD

The present invention relates to molecular conjugates, linkers for making such conjugates, methods for making the conjugates and the linkers, and methods of using the conjugates. More particularly, the present invention relates to Fc-specific antibody conjugates, hydrazide thiol linkers for preparing Fc-specific conjugates, methods for making Fc-specific conjugates, and methods of using Fc-specific antibody conjugates.

BACKGROUND

A wide variety of methods have been developed for linking molecules together to form conjugates. Of particular interest are biomolecular conjugates that are typically prepared to combine the functionalities of the joined molecules into one construct. One type of biomolecular conjugate combines a biomolecule that specifically binds to another molecule (such as a nucleic acid, an antibody, a lectin or an avidin) and a detectable label (such as a fluorescent label, fluorescent nanoparticle or an enzyme).

Conjugates of antibodies and detectable labels (antibody conjugates) can be used in immunoassays for detecting specific target molecules in biological samples. The antibody portion of such conjugates specifically binds to a target in the sample and the detectable label is utilized to provide a detectable signal that indicates the presence/and or location of the target. One type of conjugate that has become widely used, especially for immunohistochemical analysis, is a conjugate of an antibody and an enzyme (antibody-enzyme conjugate). A detectable signal is generated by adding a substrate to the sample under conditions where the enzyme portion of the antibody-enzyme conjugate converts the substrate to a detectable product (such as a colored, different-colored or fluorescent product) at the site where the antibody portion is bound to its target.

Antibody conjugates are typically prepared using coupling reagents that are characterized by having at least two reactive groups, one of which is reacted with a functional group on the antibody and the other of which is reacted with a functional group on the detectable label. However, coupling can lead to inactivation of either or both of the antibody and the detectable label. In particular, coupling can deactivate antibody-enzyme conjugates through steric effects or because the coupling reagents react with functional groups located on portions of the antibody and/or enzyme that are critical for their specificity and/or catalytic activity. Furthermore, some coupling schemes lead to conjugates that have reduced water solubility.

Coupling schemes that can provide antibody-enzyme conjugates with reduced impairment of antibody specificity and/or enzyme activity are desirable and enable greater sensitivities to be achieved in immunochemical assays such as immunohistochemical assays. Greater sensitivity is of particular importance for automated processes where additional amplification steps are undesirable.

SUMMARY

A molecular conjugate that includes a hydrazide thiol linker is disclosed. In one embodiment, an antibody-detectable label conjugate is provided including a hydrazide thiol linker covalently bonded to the Fc portion of the antibody. The Fc-specific conjugate of this embodiment provides improved detection sensitivity, thereby making immunohistochemical detection of a target molecule more amenable to automation and high-throughput applications.

Also disclosed is a method for preparing a conjugate using a hydrazide thiol linker. In one embodiment, a protecting group for a thiol group of the linker is not needed because the linker is reacted with a first molecule under conditions where the thiol group is substantially present in its neutral acid form and thus substantially unreactive. Under such conditions, a covalent bond can be formed between a hydrazide group of the linker compound and a first molecule while substantially preserving the thiol group for subsequent reaction with a thiol-reactive group of a second molecule.

Hydrazide thiol linkers and methods for making hydrazide thiol linkers also are disclosed. In addition, methods are described for using a disclosed conjugate to detect a target molecule in a sample such as a tissue section or cytology sample. The methods of detecting a target molecule can be readily automated due to the improved sensitivity exhibited by the disclosed conjugates. In certain embodiments, multiplexed assays using the disclosed conjugates are provided, for example, multiplexed assays employing disclosed antibody conjugates having fluorescent molecules or fluorescent nanoparticles as the detectable label.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF SEVERAL ILLUSTRATIVE EMBODIMENTS

Figure 1A:
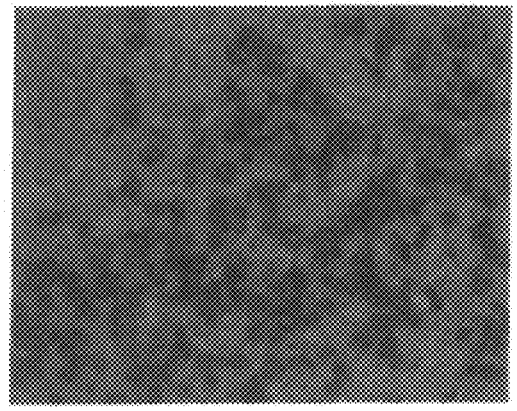
FIGS. 1A-1D are a series of images showing staining patterns for detection of Kappa in tonsil tissue using a disclosed Fc-specific antibody-alkaline phosphatase conjugate and using a streptavidin-alkaline phosphatase conjugate.
Figure 1B:
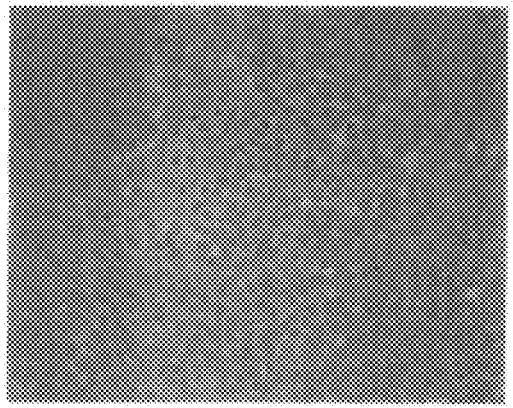
Figure 1C:
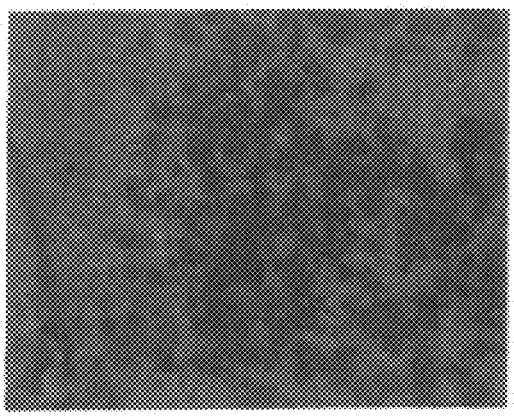
Figure 1D:
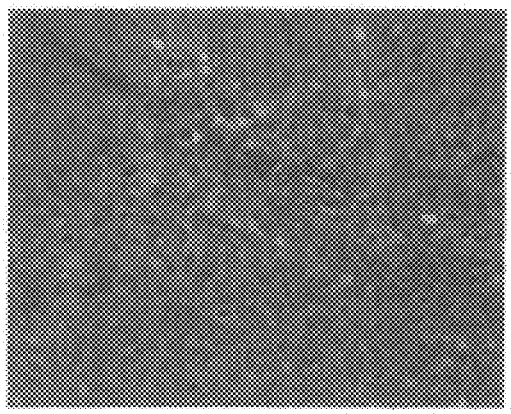
Figure 2A:
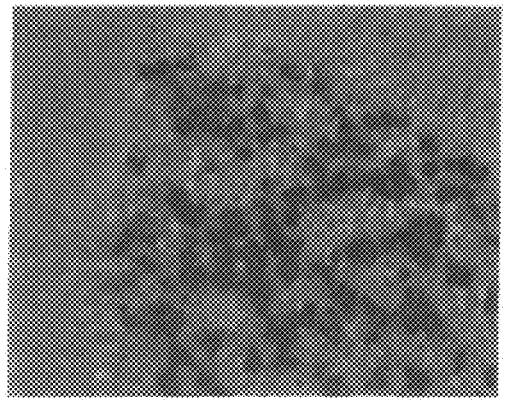
FIGS. 2A-2D are a series of images showing staining patterns for detection of Lambda in tonsil tissue using a disclosed Fc-specific antibody-alkaline phosphatase conjugate and using a streptavidin-alkaline phosphatase conjugate.
Figure 2B:
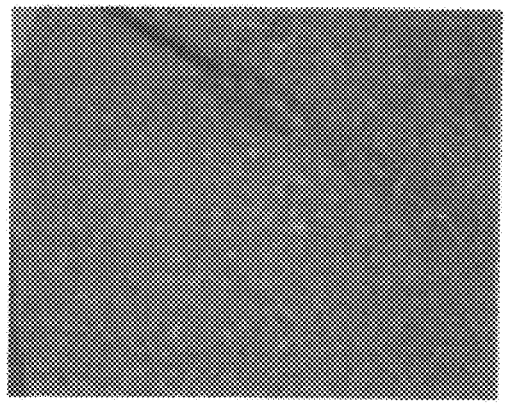
Figure 2C:
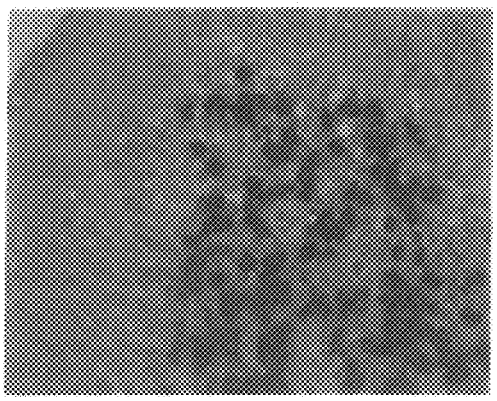
Figure 2D:
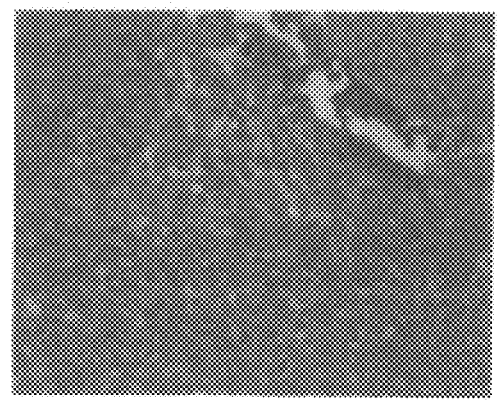
Figure 3A:
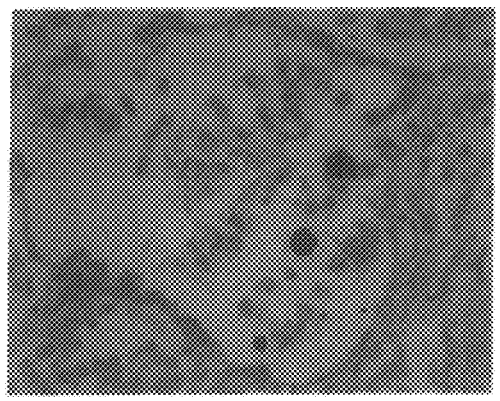
FIGS. 3A-3D are a series of images showing staining patterns for detection of CMV in lung tissue using a disclosed Fc-specific antibody-alkaline phosphatase conjugate and using a streptavidin-alkaline phosphatase conjugate.
Figure 3B:
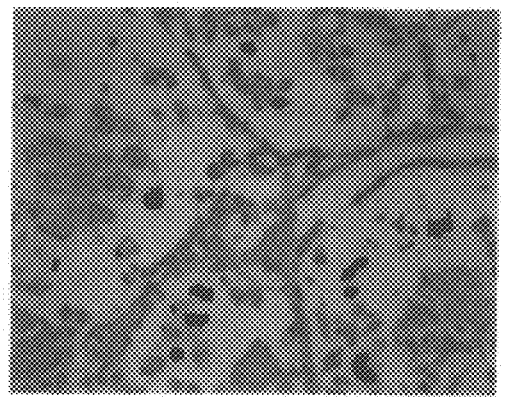
Figure 3C:
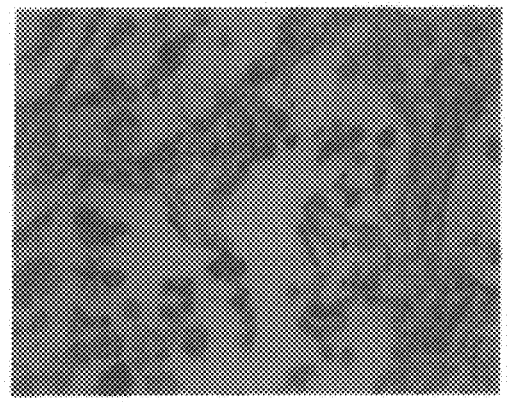
Figure 3D:
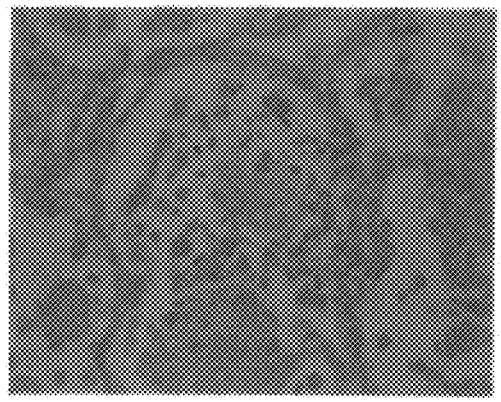
Figure 4A:
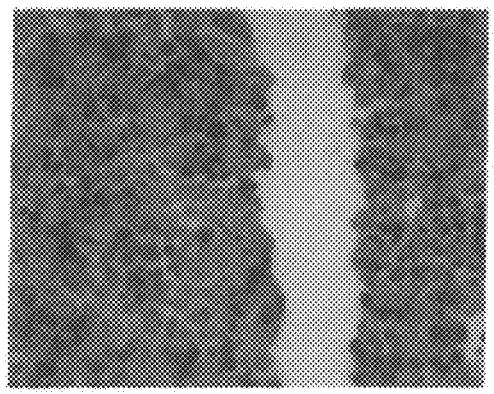
FIGS. 4A-4D are a series of images showing staining patterns for detection of EBER in spleen tissue using a disclosed Fc-specific antibody-alkaline phosphatase conjugate and using a streptavidin-alkaline phosphatase conjugate.
Figure 4B:
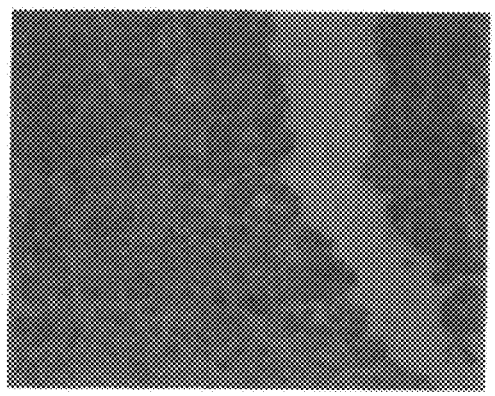
Figure 4C:
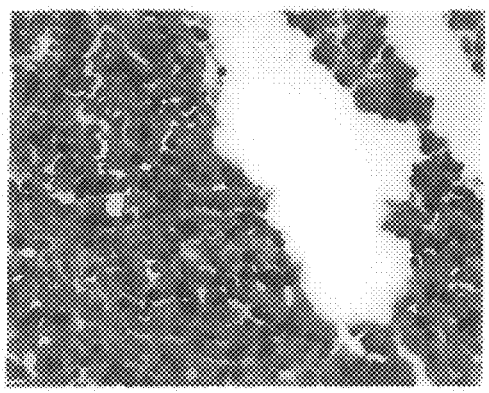
Figure 4D:
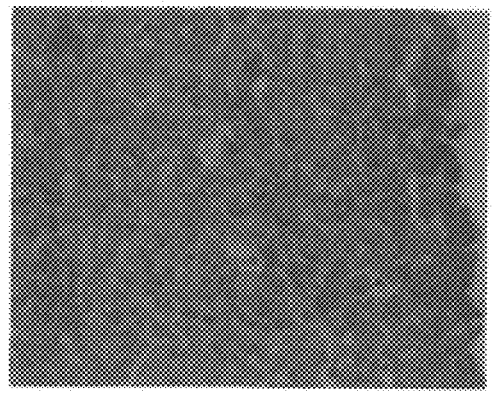

Further aspects of the invention are illustrated by the following non-limiting descriptions and examples, which proceed with respect to the abbreviations and terms below.

I. Abbreviations

Ab—antibody
(Ab-AP)—antibody-alkaline phosphatase conjugate
AP—alkaline phosphatase
BSA—bovine serum albumin
CMV—cytomegalovirus
EBER—Epstein-Barr virus early RNA
DL—detectable label
Fc—fragment crystallizable
HRP—horseradish peroxidase
IHC—immunohistochemistry
ISH—in situ hybridization
MAL—maleimide
MBCH—mercaptobutyric acid carbohydrazide
MBH—mercaptobutyric acid hydrazide
NHS—N-hydroxy-succinimide
PEG—polyethylene glycol
SBM—specific binding molecule

II. Terms

The terms "a," "an" and "the" include both singular and plural referents unless the context clearly indicates otherwise.

The term "amination" as used herein refers to reaction of a carbonyl group of an aldehyde or a ketone with an amine group, wherein an amine-containing compound such as an amine or a hydrazide reacts with the aldehyde or ketone to first form a Shiff base that can then reversibly rearrange to a more stable form, or optionally be reduced to prevent reversal of the reaction. "Reductive amination" conditions include addition of a reducing agent, more typically addition of a mild reducing agent such as sodium cyanoborohydride or one of its co-geners, for example, sodium triacetoxyborohydride. Other mild reducing agents that can be employed include various amine boranes.

The term "antibody" collectively refers to an immunoglobulin or immunoglobulin-like molecule (including IgA, IgD, IgE, IgG and IgM, and similar molecules produced during an immune response in any organism, for example, in mammals such as humans, goats, rabbits and mice), or a fragment thereof, that specifically binds to a target (or a group of highly similar targets) to the substantial exclusion of binding to other molecules. In some embodiments, an antibody specifically binds to a target with a binding constant that is at least $10^3$ $M^{-1}$ greater, $10^4$ $M^{-1}$ greater or $10^5$ $M^{-1}$ greater than a binding constant for other molecules in a sample. In other embodiments, an antibody has a Kd value for binding to an antigenic determinant (such as a hapten or epitope) that is on the order of $10^{-6}$ M or lower, such as $10^{-9}$ M or lower, or even $10^{-12}$ M or lower. Kd values can, for example, be determined by competitive ELISA (enzyme-linked immunosorbent assay) or using a surface-plasmon resonance device such as the Biacore T100, which is available from Biacore, Inc., Piscataway, N.J. Antibody fragments include proteolytic antibody fragments [such as F(ab')$_2$ fragments, Fab' fragments, Fab'-SH fragments and Fab fragments as are known in the art], recombinant antibody fragments (such as sFv fragments, dsFv fragments, bispecific sFv fragments, bispecific dsFv fragments, diabodies, and triabodies as are known in the art), and camelid antibodies (see, for example, U.S. Pat. Nos. 6,015,695; 6,005,079; 5,874,541; 5,840,526; 5,800,988; and 5,759,808). Antibodies include both monoclonal and polyclonal antibody preparations. Although an antibody of a disclosed conjugate can specifically bind any particular molecule or any particular group of highly similar molecules, in particular embodiments, the antibody comprises an anti-hapten antibody (which can, for example, be used to detect a hapten-labeled probe sequence directed to a nucleic acid sequence of interest). In particular embodiments, the antibody comprises an anti-antibody antibody that can be used as a secondary antibody in an immunoassay. For example, the antibody can comprise an anti-IgG antibody such as an anti-mouse IgG antibody, an anti-rabbit IgG antibody or an anti-goat IgG antibody.

The phrase "conditions where a thiol group of a hydrazide thiol linker is substantially present in its neutral acid form" refers to conditions, such as conditions of pH, wherein less than about 1% of the thiol group (—SH; the protonated neutral acid form) of the linker is present in its conjugate base form (—S$^-$; unprotonated, negatively charged form). For example, under such conditions less than about 0.1%, less than about 0.01%, or even less than about 0.001% of the linker can be in the conjugate base form. Conditions where the thiol group of the hydrazide thiol linker compound is substantially present in its neutral acid form include a pH of less than about 7, for example, a pH of less than about 6 such as a pH of less than about 5.5. In particular embodiments, such conditions include a range of pHs, for example, from a pH of about 3 to a pH of about 7, from a pH of about 4 to a pH of about 7, from a pH of about 4 to a pH of about 6, from a pH of about 4.5 to a pH of about 5.5, or any sub-range of each of these ranges. In other embodiments, the upper limit of the pH range in which a thiol group of a particular linker is substantially present in its neutral acid form (less than 1% of the thiol group being present as the conjugate base form) can be higher than 7, such as a pH of 8. One of ordinary skill in the art can readily determine an upper limit to the pH range in which a given thiol group will be substantially present in the neutral acid form using the Henderson-Hasselbach equation and a pKa value for a thiol group of the linker. In yet other embodiments, a thiol group of a particular linker can be substantially present in its neutral acid form in a solvent system for which an accurate pH cannot be determined, and one of ordinary skill in the art will recognize that solvent systems that are less polar than water may help keep the thiol group in its neutral acid form at higher apparent pHs. Alternatively, an experimental determination of whether under particular conditions a thiol group of a linker is substantially present in its neutral acid form can be made by determining whether the thiol will reduce a disulfide bond present in another molecule. For example, a determination can be made of the number of free thiol groups (for example, using Ellman's reagent) introduced into a molecule having disulfides (such as an immunoglobulin) by contact with the linker under the particular conditions of pH (or estimated pH for non-aqueous systems). Addition of an excess of the hydrazide thiol linker (such as a 50-fold excess or more) over a period of time (such as an hour or more) can be followed by the determination of the average number of free thiols introduced into the molecule. If free thiols are generated to a substantial degree (such as greater than an average of two thiols introduced per immunoglobulin molecule), it shows that the thiol of the linker is not substantially present in it neutral acid form under the tested conditions. For example, at a pH of about 7, a one hundred-fold excess of the linker MBH relative to an immunoglobulin will produce an average of about 2 thiols per immunoglobulin molecule. At a lower pH of 5, a thousand-fold excess of the MBH linker will produce, on average, substantially less than 1 thiol per immunoglobulin in 24 hours. These results demonstrate that for the linker MBH, the thiol group is substantially present in its neutral acid form at a pH of about 7 or lower, since as pH is lowered, the equilibrium between the neutral acid form and its conjugate base is shifted more towards the neutral acid form.

A "conjugate" refers to two or more molecules (and/or materials such as nanoparticles) that are covalently linked into a larger construct. In some embodiments, a conjugate includes one or more biomolecules (such as peptides, nucleic acids, proteins, enzymes, sugars, polysaccharides, lipids, glycoproteins, and lipoproteins) covalently linked to one or more other molecules, such as one or more other biomolecules. In other embodiments, a conjugate includes one or more specific-binding molecules (such as antibodies and nucleic acid sequences) covalently linked to one or more detectable labels (such as fluorescent molecules, fluorescent nanoparticles, haptens, enzymes and combinations thereof).

A "detectable label" is a molecule or material that can produce a detectable (such as visually, electronically or otherwise) signal that indicating the presence and/or concentration of the label in a sample. When conjugated to a specific binding molecule, the detectable label can be used to locate and/or quantify the target to which the specific binding molecule is directed. Thereby, the presence and/or concentration of the target in a sample can be detected by detecting the signal produced by the detectable label. A detectable label can be detected directly or indirectly, and several different detectable labels conjugated to different specific-binding molecules can be used in combination to detect one or more targets. For example, a first detectable label such as a hapten conjugated to a nucleic acid probe or antibody specific to a target can be detected indirectly through the use of a second detectable label that is conjugated to a molecule that specifically binds the first detectable label. Multiple detectable labels that can be separately detected can be conjugated to different specific binding molecules that specifically bind different targets to provide a multiplexed assay that can provide simultaneous detection of the multiple targets in a sample. A detectable signal can be generated by any known or yet to be discovered mechanism including absorption, emission and/or scattering of a photon (including radio frequency, microwave frequency, infrared frequency, visible frequency and ultra-violet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. Particular examples of detectable labels include enzymes such as horseradish peroxidase, alkaline phosphatase, acid phosphatase, glucose oxidase, β-galactosidase, β-glucuronidase or β-lactamase; fluorescent molecules such as fluoresceins, coumarins, BODIPY dyes, resorufins, and rhodamines (many additional examples of fluorescent molecules can be found in *The Handbook—A Guide to Fluorescent Probes and Labeling Technologies*, Molecular Probes, Eugene, Oreg.); nanoparticles such as quantum dots (obtained, for example, from QuantumDot Corp, Invitrogen Nanocrystal Technologies, Hayward, Calif.; see also, U.S. Pat. Nos. 6,815,064, 6,682596 and 6,649,138, each of which patents is incorporated by reference herein); metal chelates such as DOTA and DPTA chelates of radioactive or paramagnetic metal ions like $Gd^{3+}$; and liposomes, for example, liposomes containing trapped fluorescent molecules. Where the detectable label includes an enzyme, a detectable substrate such as a chromogen, a fluorogenic compound, or a luminogenic compound can be used in combination with the enzyme to generate a detectable signal (A wide variety of such compounds are commercially available, for example, from Invitrogen Corporation, Eugene Oreg.). Particular examples of chromogenic compounds include diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet. Alternatively, an enzyme can be used in a metallographic detection scheme. Metallographic detection methods include using an enzyme such as alkaline phosphatase in combination with a water-soluble metal ion and a redox-inactive substrate of the enzyme. The substrate is converted to a redox-active agent by the enzyme, and the redox-active agent reduces the metal ion, causing it to form a detectable precipitate. (See, for example, co-pending U.S. patent application Ser. No. 11/015,646, filed Dec. 20, 2004, PCT Publication No. 2005/003777 and U.S. Patent Application Publication No. 2004/0265922; each of which is incorporated by reference herein). Metallographic detection methods include using an oxido-reductase enzyme (such as horseradish peroxidase) along with a water soluble metal ion, an oxidizing agent and a reducing agent, again to for form a detectable precipitate. (See, for example, U.S. Pat. No. 6,670,113, which is incorporated by reference herein). Haptens are small molecules that are specifically bound by antibodies, although by themselves they will not elicit an immune response in an animal and must first be attached to a larger carrier molecule such as a protein or a poly-nucleic acid to generate an immune response. Examples of haptens include di-nitrophenol, biotin, digoxigenin, and fluorescein. Additional examples of oxazole, pyrazole, thiazole, nitroaryl, benzofuran, triperpene, urea, thiourea, rotenoid, coumarin and cyclolignan haptens are disclosed in co-pending U.S. Provisional Patent Application No., 60/856,133, filed Nov. 1, 2006, which is incorporated by reference herein.

The term "Fc-specific conjugate" as used herein refers to a conjugate of an immunoglobulin (or fragment thereof) in which a second molecule (such as a detectable label) is covalently bonded to the glycosylated portion of the immunoglobulin (or a fragment of an immunoglobulin that retains the glycosylated portion). The glycosylated portion of an immunoglobulin is found in the Fc-region, which is a region of an immunoglobulin that is located on the heavy chains of the immunoglobulin at positions outside of the portion of the immunoglobulin that is responsible for the specific binding activity of the immunoglobulin.

The term "hydrazide group" refers to a hydrazide group (—CO—NH—NH$_2$); a carbohydrazide group (—NH—NH—CO—NH—NH$_2$); a semicarbazide group (—NH—CO—NH—NH$_2$); a thiosemicarbazide group (—NH—CS—NH—NH$_2$); a thiocarbazide group (—NH—NH—CS—NH—NH$_2$); a carbonic acid dihydrazine group (—NH—CO—NH—NH—CO—NH—NH$_2$) or a sulfur containing derivative thereof; or a hydrazine carboxylate group (—O—CO—NH—NH$_2$) or a sulfur-containing derivative thereof.

The term "hydrazide-reactive group" refers to a group of atoms that can react with and form a covalent bond to a hydrazide group. Aldehyde and ketone groups are examples of hydrazide-reactive groups. Hydrazide-reactive groups can be an intrinsic part of a molecule or can be introduced to a molecule. One method for introducing an aldehyde group (a hydrazide-reactive group) into polysaccharides and glycoproteins (including antibodies) is by oxidation such as periodate-mediated oxidation of vicinal diols. In addition, double bonds in unsaturated fatty acids and ceramides can be converted to diols by osmium tetroxide and then oxidized by periodate to aldehydes. Furthermore, N-terminal serine and threonine residues of peptides and proteins can be selectively oxidized by periodate to aldehyde groups, permitting selective modification of certain proteins such as corticotrophin and β-lactamase. Modification of periodate-oxidized antibodies does not typically inactivate the antibody. Varying the concentration of sodium periodate during the oxidation reaction gives some specificity with regard to the types of sugar residues that are modified. For example, sodium periodate at a concentration of 1 mM at 0° C. typically cleaves only at the adjacent hydroxyls between carbon atoms 7, 8 and 9 of sialic acid residues. Oxidizing polysaccharides using 10 mM or greater concentrations of sodium periodate results in oxidation of sugar residues other than sialic acid, thereby creating many aldehydes on a given polysaccharide. A suitable general protocol is described by Hermanson, "Bioconjugate Techniques," Academic Press, San Diego, 1996, ISBN 0-12-342336-8, which is incorporated by reference herein. Another method for introducing aldehydes into biomolecules is through the use of specific sugar oxidases, for example, galactose oxidase, which is an enzyme that oxidizes terminal galactose residues to aldehydes, particularly in glycoproteins. When galactose residues are penultimate to sialic acid residues, neuramidase can be used to remove the sialic acid residue and expose galactose as the terminal residue. A protocol for using a combination of neuramidase and galactose oxidase to oxidize galactose residues to provide a reactive aldehyde group is provided in Hermanson, "Bioconjugate Techniques," Academic Press, San Diego, 1996, ISBN 0-12-342336-8, which is incorporated by reference herein. Aldehydes also can be introduced to a molecule by reacting an amine group of a molecule with an NHS-aldehyde such as succinimidyl p-formylbenzoate (SFB) or succinimidyl p-formylphenoxyacetate (SFPA) (Invitrogen Corp., Eugene, Oreg.). Alternatively, bis-aldehyde compounds such as glutaraldehyde can be used to modify an amine group to provide an aldehyde group. Again, suitable protocols are provided in Hermanson, "Bioconjugate Techniques," Academic Press, San Diego, 1996, ISBN 0-12-342336-8, which is incorporated by reference herein.

The term "hydrazide thiol linker" refers to a molecule including one or more hydrazide groups and one or more thiol groups (—SH) joined covalently through one or more linking atoms. The hydrazide group(s) and thiol group(s) of a hydrazide thiol linker can be joined through one or more of various groups of atoms including methylene groups (—CH$_2$—), branched alkylene groups, additional hydrazide groups, aromatic groups, heteroaromatic groups, alicyclic groups, polyalkylene glycol groups (such as ethylene oxide groups; —O—CH$_2$—CH$_2$—), amide groups (—CONH—), amine groups (—NH—), ether groups (—O—), and combinations thereof. A "PEG-based hydrazide thiol linker" refers to a linker including 1 or more ethylene glycol groups as part of its structure. A "multifunctional hydrazide thiol linker" refers to a branched linker having at least one hydrazide group, at least one thiol group, and at least one additional reactive group, such as an additional hydrazide group, an additional thiol group, or any other group useful for preparing molecular conjugates. In some embodiments, a PEG-based hydrazide thiol linker comprises a discrete PEG (dPEG) linker, which can be made from dPEG starting materials such as those disclosed in U.S. Patent Application Publication No. 20060020134, and can be purchased from Quanta Biodesign (Powell, Ohio). Examples of additional reactive groups that can be included in a polyfunctional hydrazide-thiol linker include maleimide groups and active esters, such as N-hydroxysuccinimide esters, and hydroxy groups (—OH). Additional examples of reactive groups can be found in Hermanson, "Bioconjugate Techniques," Academic Press, San Diego, 1996, ISBN 0-12-342336-8, which is incorporated by reference herein.

The term "sample" refers to any liquid, semi-solid or solid substance (or material) in or on which a target can be present. In particular, a sample can be a biological sample or a sample obtained from a biological material. Examples of biological samples include tissue samples and cytology samples.

The term "specific binding molecule" refers to a molecule that specifically binds to a second molecule. "Specifically binds" means that the specific-binding molecule binds to the second molecule to the substantial exclusion of other molecules that are present in a sample (for example, the binding constant of the specific-binding molecule is at least $10^2$ M$^{-1}$ greater, $10^3$ M$^{-1}$ greater, $10^4$ M$^{-1}$ greater or $10^5$ M$^{-1}$ greater than a binding constant for other molecules in the sample). Examples of specific binding molecules include nucleic acids, receptors, antibodies, enzymes, lectins and avidins. Examples of specific-binding interactions in which specific binding molecules can participate include formation of duplexes and triplexes of nucleic acid sequences, receptor-ligand interactions (such as folate-folate receptor interactions), antibody-antigen interactions, enzyme-substrate interactions, lectin-sugar reactions and avidin-biotin interactions (such as streptavidin-biotin interactions).

The term "target" refers to any molecule for which the presence, location and/or concentration is or can be determined. Examples of target molecules include proteins, nucleic acid sequences, and haptens, such as haptens covalently bonded to nucleic acid sequences or proteins. Target molecules are typically detected using one or more conjugates of a specific binding molecule and a detectable label.

The term "thiol-reactive group" refers to an atom or atoms that can react with and form a covalent bond with a thiol group. A thiol reactive group can be an intrinsic part of a molecule or can be introduced to the molecule through reaction with one or more other molecules. Examples of thiol-reactive groups include non-polymerizable Michael acceptors, haloacetyl groups (such as bromoacetyl and iodoacetyl groups), alkyl halides, maleimides, aziridines, acryloyl groups, vinyl sulfones, benzoquinones, aromatic groups that can undergo nucleophilic substitution such as fluorobenzene groups (such as tetra and pentafluorobenzene groups), and disulfide groups such as pyridyl disulfide groups and thiols activated with Ellman's reagent. Additional examples of each of these types of groups will be apparent to those skilled in the art. Further examples and information regarding reaction conditions and methods for exchanging one type of reactive group for another to add a thiol-reactive group are provided in Hermanson, "Bioconjugate Techniques," Academic Press, San Diego, 1996, ISBN 0-12-342336-8, which is incorporated by reference herein. In a particular embodiment, a heterobifunctional linker molecule is attached to a molecule to introduce a thiol-reactive group. For example, a linker having a maleimide group and an N-Hyroxysuccinimide (NHS) group can be attached to an amine group on a molecule through the NHS group, thereby providing the molecule with a thiol-reactive maleimide group that can be reacted with a thiol group on another molecule (such as one introduced using a hydrazide thiol linker and the disclosed method) to form a conjugate.

III. Overview

One of ordinary skill in the art will recognize that the disclosed method can be used to join any combination of molecules having functional groups that can react with a hydrazide thiol linker. The non-limiting description that follows focuses on antibody conjugates, and more particularly, on antibody-enzyme conjugates, but should not be construed as a limitation on the scope of the invention. Although the specifically disclosed conjugates are antibody-enzyme conjugates, conjugates between other biomolecules (such as nucleic acid sequences) and other detectable labels (such as haptens, fluorescent labels, fluorescent nanoparticles and fluorescent proteins, such as green fluorescent protein) are contemplated and fall within the scope of the disclosure.

Accordingly, in one aspect, a method is disclosed for forming a conjugate of two or more molecules. The method includes reacting a hydrazide thiol linker with a first molecule (such as an antibody) having a hydrazide-reactive group (such as an aldehyde) to form a thiolated first molecule. The reaction is carried out under conditions where a thiol group of the hydrazide thiol linker is substantially present in its neutral acid (protonated) form. The thiolated first molecule can then be reacted with a second molecule having a thiol-reactive group (such as a maleimide group introduced to the second molecule) to form the conjugate. In a particular embodiment, the reaction of the first molecule with the linker is carried out at a pH from about pH=4 to about pH=7. In other particular embodiments, the hydrazide thiol linker can be a PEG-based hydrazide thiol linker, a multifunctional hydrazide thiol linker, or a PEG-based multifunctional hydrazide thiol linker.

In another embodiment, the method can be used to covalently join a specific binding molecule to a detectable label. In a more particular embodiment, the method can be used to link a first molecule having a glycosylated portion to another molecule. In this embodiment, the glycosylated portion is first oxidized to generate an aldehyde group that can be reacted with a hydrazide thiol linker. In an even more particular embodiment, the glycosylated first molecule can be an antibody that has a glycosylated Fc region. An Fc-specific thiolated antibody is formed by reaction with a hydrazide thiol linker, and the Fc-specific thiolated antibody can be reacted with a detectable label having a thiol-reactive group.

In another aspect, a variety of hydrazide thiol linkers and methods for making the same are provided as outlined in the Synthetic Overview and specific Examples that follow. A further aspect is a conjugate prepared with a disclosed linker. In an additional aspect, a kit is disclosed that includes a disclosed linker and instructions for performing the disclosed method for making a conjugate. Also disclosed are methods for using disclosed conjugates to detect a target in a sample.

IV. Synthetic Overview

A. Preparation of Hydrazide Thiol Linkers

Although any hydrazide thiol linker can be used in the disclosed method of making a conjugate, in one embodiment, a hydrazide thiol linker can be provided by reacting a thiolactone with hydrazine, carbohydrazide or a dihydrazide according to Scheme 1 below, wherein n=1, 2 or 3, $R_1$ is H, —CONHNH$_2$, or —CO-A-CONHNH$_2$, where A is a divalent group having between 1 and 100 carbon atoms that can be interrupted by one or more heteroatoms (for example, O, N or S), and can be substituted, for example, with one or more alkyl, hydroxyl, alkoxy, acyl, carboxy, halogen, sulfonate, oxo, phosphonate and/or amine groups. In more particular embodiments, A is a divalent group consisting of 1-10 methylene groups (—CH$_2$—) and/or 1-24 ethylene oxide (—CH—CH$_2$—O—) groups. In even more particular embodiments, A is a divalent group consisting of 1-6 methylene groups or 4-12 ethylene oxide groups.

Scheme 1

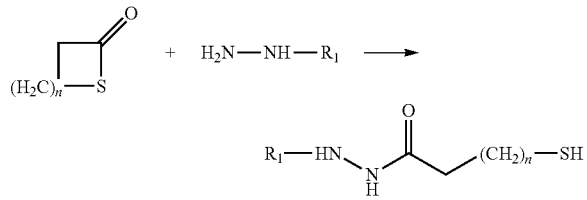

A wide variety of hydrazide thiol linkers that can be used in the disclosed method also can be provided according to scheme 2 below. In this scheme, Z is a divalent group having from 1 to 100 carbon atoms, wherein the divalent group can be interrupted by one or more heteroatoms (for example, O, N or S), and can be substituted, for example, with one or more hydroxyl, alkoxy, acyl, carboxy, halogen, sulfonate, oxo, phosphonate and/or amine groups. In more particular embodiments, Z is a divalent group consisting of 1-10 methylene groups (—CH$_2$—) and/or 1-24 ethylene oxide (—CH—CH$_2$—O—) groups. In even more particular embodiments, Z is a divalent group consisting of 1-6 methylene groups or 4-12 ethylene oxide groups. $R_2$ is H, —CONHNH$_2$, or —CO-A-CONHNH$_2$, where A is a divalent group having between 1 and 100 carbon atoms that can be interrupted by one or more heteroatoms (for example, 0, N or S), and can be substituted, for example, with one or more alkyl, hydroxyl, alkoxy, acyl, carboxy, halogen, sulfonate, oxo, phosphonate and/or amine groups.

Scheme 2

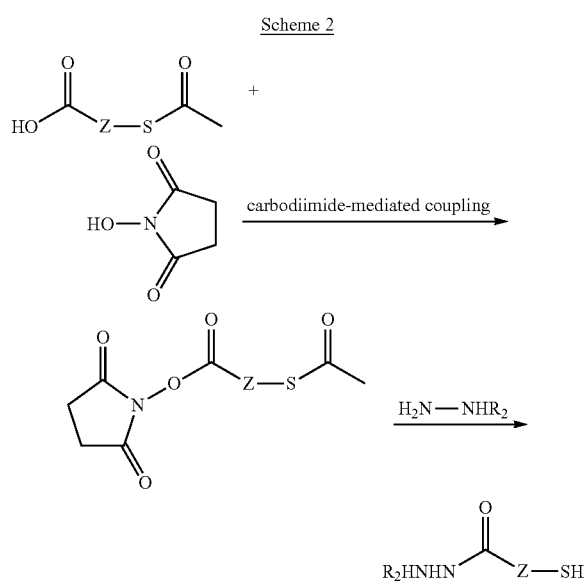

In some embodiments, a PEG-based hydrazide thiol linker that can be used in the disclosed method is provided and is prepared according to scheme 3. In scheme 3, m=2 to 50; $R_3$ is H, —CONHNH$_2$, or —CO-A-CONHNH$_2$, where A is a divalent group having between 1 and 100 carbon atoms that can be interrupted by one or more heteroatoms (for example, O, N or S), and can be substituted, for example, with one or more alkyl, hydroxyl, alkoxy, acyl, carboxy, halogen, sulfonate, oxo, phosphonate and/or amine groups; and X and Y are independently a bond or a divalent group having 1 to 20 carbon atoms. In more particular embodiments, A is a divalent group consisting of 1-10 methylene groups (—CH$_2$—) and/or 1-24 ethylene oxide (—CH—CH$_2$—O—) groups. In even more particular embodiments, A is a divalent group consisting of 1-6 methylene groups or 4-12 ethylene oxide groups. The X and Y divalent groups can be interrupted by one or more heteroatoms (for example, O, N or S), and can be substituted, for example, with one or more alkyl, hydroxyl, alkoxy, acyl, carboxy, halogen, sulfonate, oxo, phosphonate and/or amine groups. In more particular embodiments, X and Y are independently a bond or —(CH$_2$)$_p$— where p=1 to 3. The carbodiimide used in the coupling reaction can be any carbodiimide that provides the desired coupling according to the scheme. Examples of suitable carbodiimides include DCC (N,N'-dicyclohexylcarbodiimide), and DIC (N,N'-diisopropylcarbodiimide). In a working embodiment that is discussed below, DCC is used to accomplish the coupling.

Scheme 3

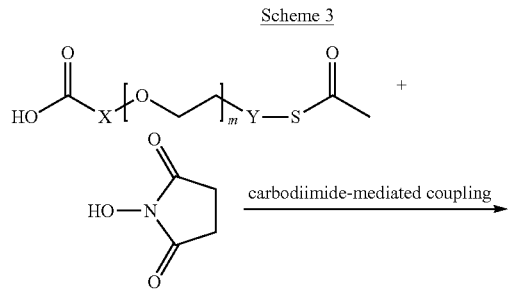

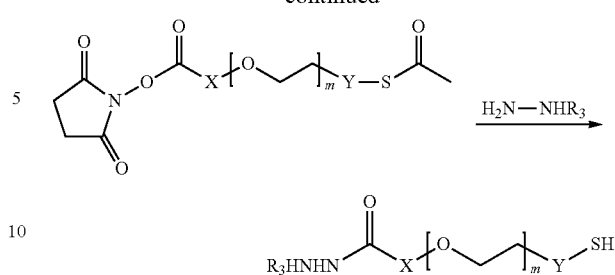

In other embodiments, a multifunctional hydrazide thiol linker that can be used in the disclosed method is provided. Schemes 4a, 4b, 4c, and 4d below show general methods for preparing multifunctional linkers from homocysteine, lysine, glutamic acid and homoserine, respectively. In Schemes 4a, 4b, 4c and 4d, D is a divalent group having from 1 to 100 carbon atoms, wherein the divalent group can be interrupted by one or more heteroatoms (for example, O, N or S), and can be substituted, for example, with one or more alkyl, hydroxyl, alkoxy, acyl, carboxy, halogen, sulfonate, oxo, phosphonate and/or amine groups. In more particular embodiments, D is a divalent group consisting of 1-10 methylene groups (—CH$_2$—) and/or 1-24 ethylene oxide (—CH—CH$_2$—O—) groups. In even more particular embodiments, D is a divalent group consisting of 1-6 methylene groups or 4-12 ethylene oxide groups. Also in Schemes 4a, 4b, 4c and 4d, $R_4$ is H, —CONHNH$_2$, or —CO-A-CONHNH$_2$, where A is a divalent group having between 1 and 100 carbon atoms that can be interrupted by one or more heteroatoms (for example, O, N or S), and can be substituted, for example, with one or more alkyl, hydroxyl, alkoxy, acyl, carboxy, halogen, sulfonate, oxo, phosphonate and/or amine groups. In more particular embodiments, A is a divalent group consisting of 1-10 methylene groups (—CH$_2$—) and/or 1-24 ethylene oxide (—CH—CH$_2$—O—) groups. In even more particular embodiments, A is a divalent group consisting of 1-6 methylene groups or 4-12 ethylene oxide groups.

Scheme 4a

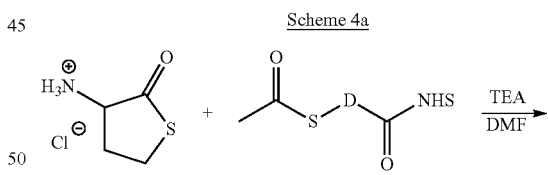

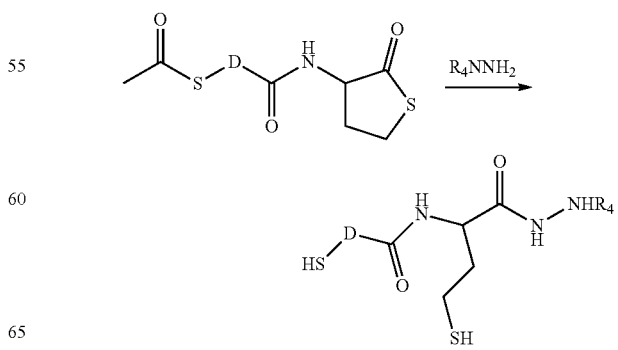

Scheme 4b

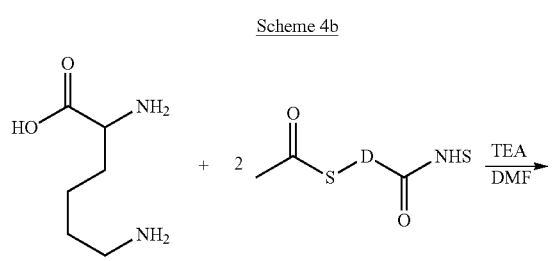

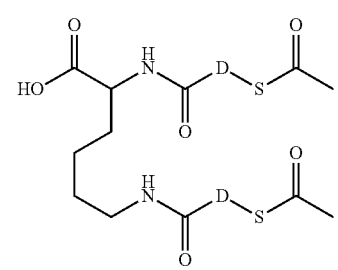

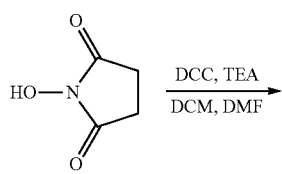

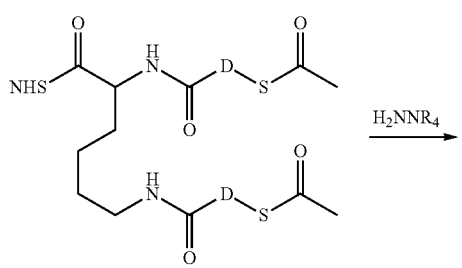

Scheme 4c

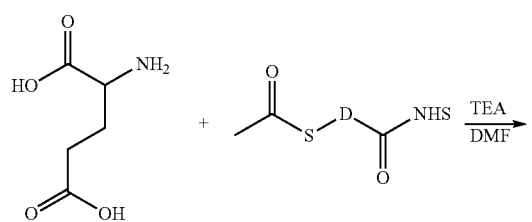

-continued

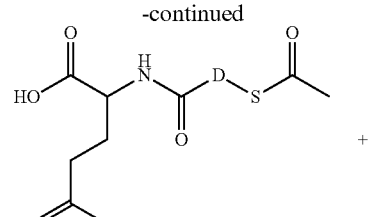

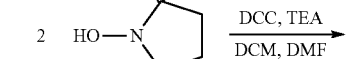

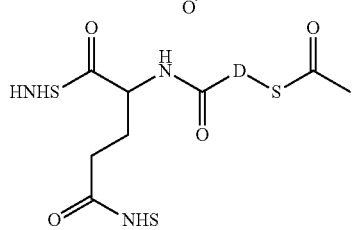

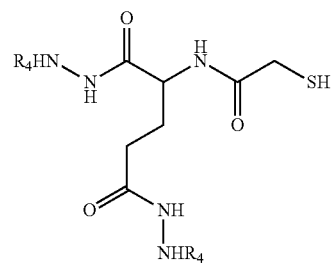

Scheme 4d

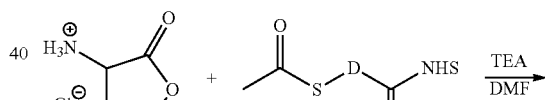

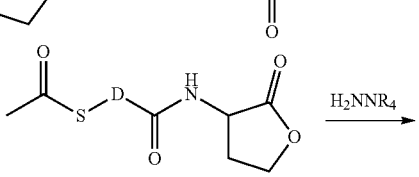

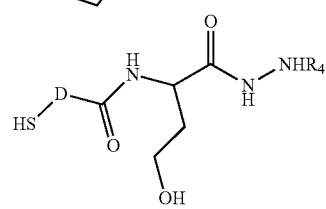

In other particular embodiments, a PEG-based multifunctional hydrazide thiol linker that can be used in the disclosed method is provided. Schemes 5a, 5b and 5c illustrate general synthetic schemes that can be used to provide such linkers. In these schemes, p=2 to 50 and $R_5$ is H, —CONHNH$_2$, or —CO-A-CONHNH$_2$, where A is a divalent group having between 1 and 100 carbon atoms that can be interrupted by one or more heteroatoms (for example, O, N or S), and can be substituted, for example, with one or more alkyl, hydroxyl, alkoxy, acyl, carboxy, halogen, sulfonate, oxo, phosphonate and/or amine groups. In more particular embodiments, A is a divalent group consisting of 1-10 methylene groups (—CH$_2$—) and/or 1-24 ethylene oxide (—CH—CH$_2$—O—) groups. In even more particular embodiments, A is a divalent group consisting of 1-6 methylene groups or 4-12 ethylene oxide groups. R$_7$ can be H, alkyl or a protecting group.
Scheme 5a
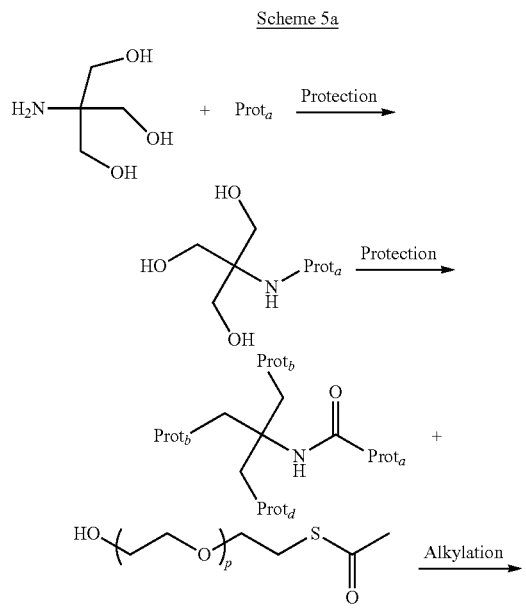
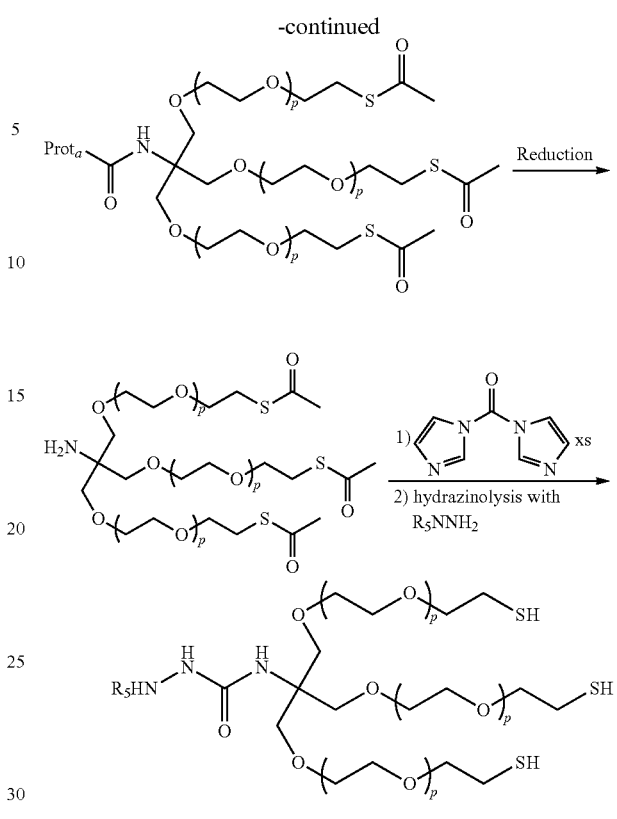
Scheme 5b
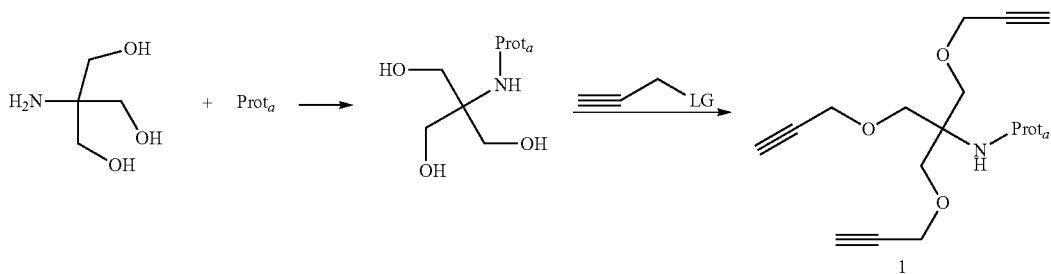
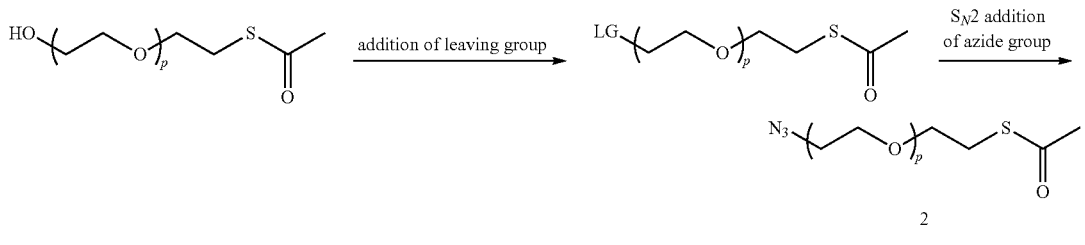

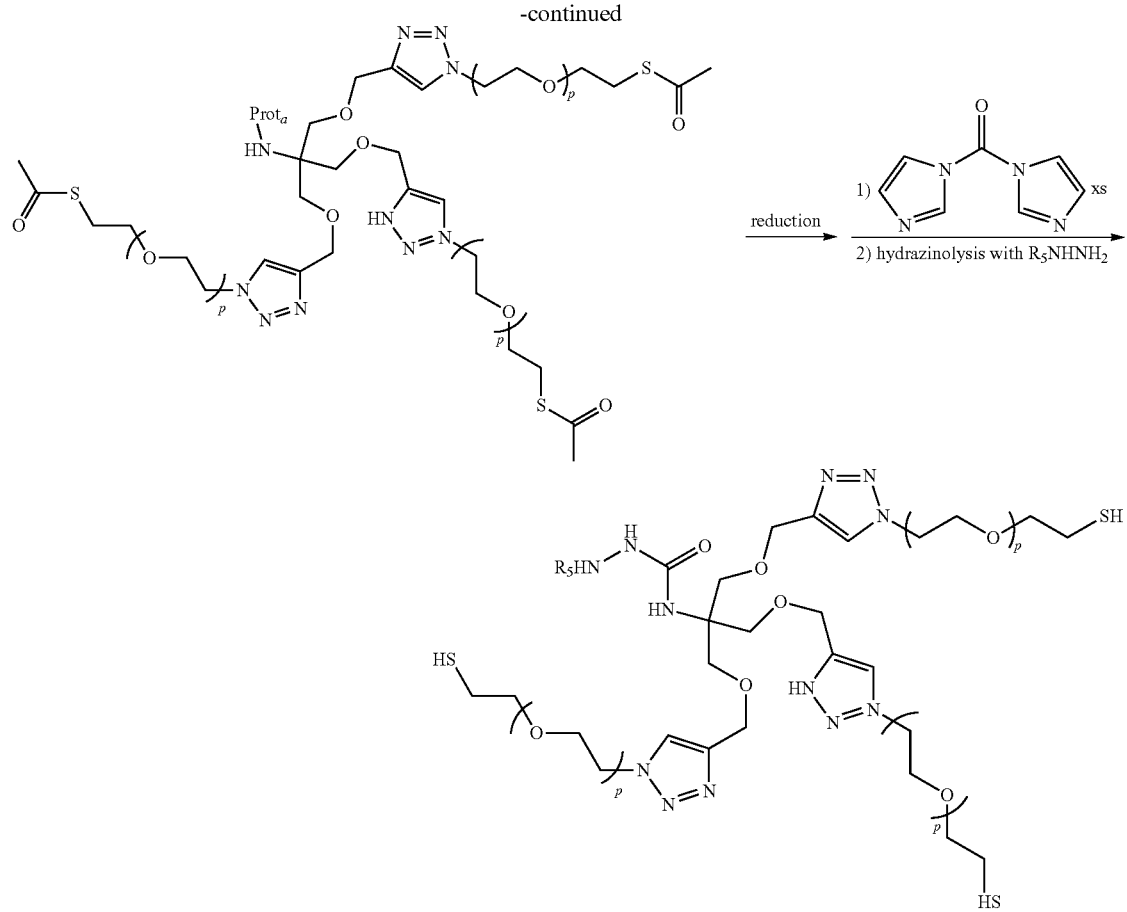

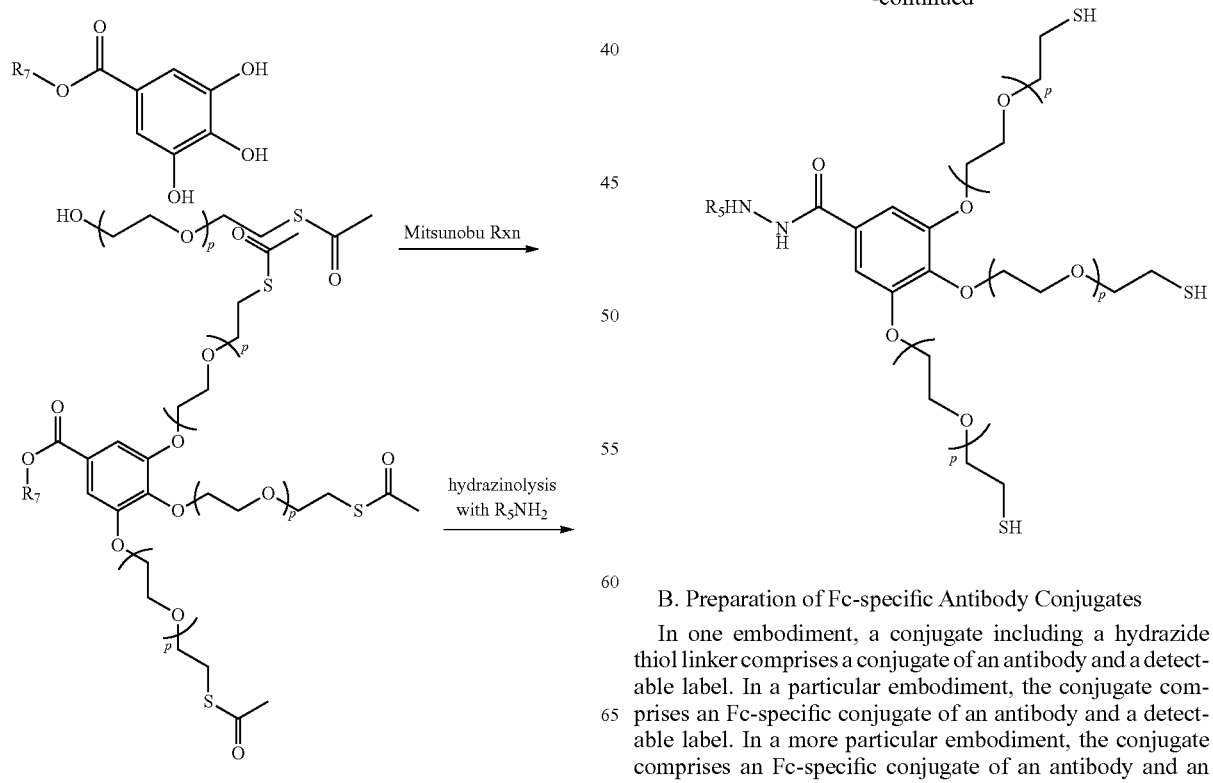

B. Preparation of Fc-specific Antibody Conjugates

In one embodiment, a conjugate including a hydrazide thiol linker comprises a conjugate of an antibody and a detectable label. In a particular embodiment, the conjugate comprises an Fc-specific conjugate of an antibody and a detectable label. In a more particular embodiment, the conjugate comprises an Fc-specific conjugate of an antibody and an enzyme such as alkaline phosphatase. Scheme 6 illustrates a method of adding a hydrazide thiol linker to an antibody in an Fc-specific manner.

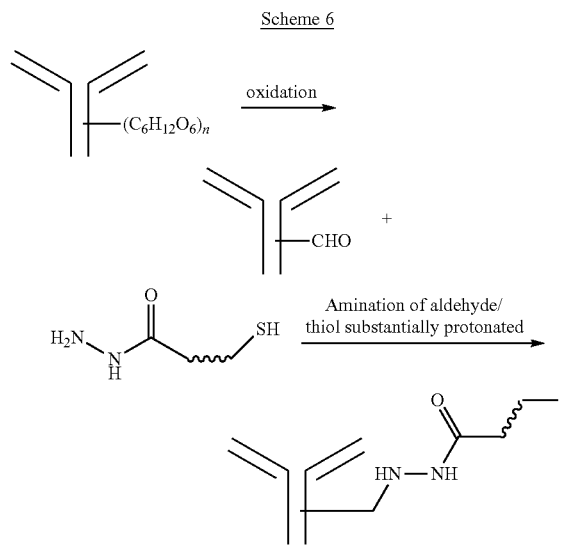

In Scheme 6, an antibody having a glycosylated Fc-portion is site-specifically oxidized to generate one or more aldehyde groups in the sugar moieties of the glycosylated Fc-portion. The aldehyde group(s) is (are) then reacted with a hydrazide thiol linker under conditions where the thiol group of the hydrazide thiol linker is substantially protonated (substantially in its neutral acid form). Under such conditions, the hydrazide group of the linker is covalently bonded to the Fc-portion of the antibody while leaving the thiol group substantially unreacted (such as substantially unreacted with disulfide linkages in the antibody) and thus retained for later reaction with a second molecule having a thiol-reactive group such as a detectable label having a thiol-reactive group. The reaction desirably includes further reaction with a mild reductant (an example of a reductive amination) to form a more stable hydrazone. Coupling of the thiolated antibody with a detectable label having a thiol-reactive group (such as a maleimide group) is illustrated in Scheme 7.

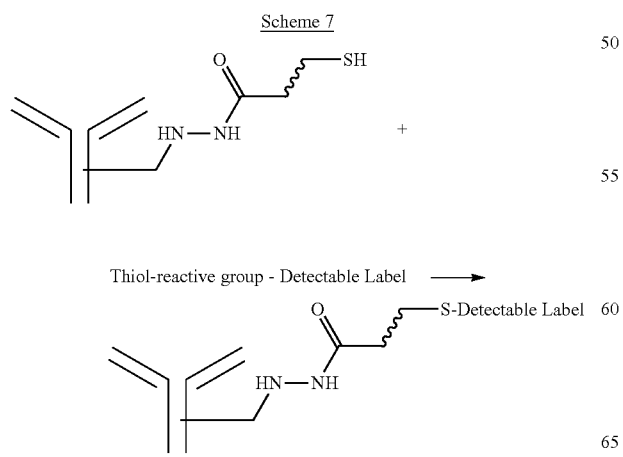

V. EXAMPLES

The following non-limiting examples of working embodiments are provided to further illustrate certain aspects of the invention.

Example 1

Synthesis of Mercaptobutyric Acid Hydrazide (MBH)

In a particular working embodiment, a hydrazide thiol linker was prepared from γ-butyrothiolactone according to Scheme 8.

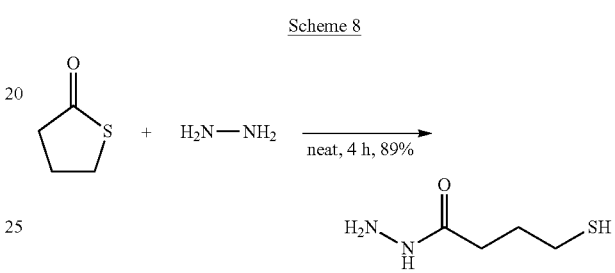

In particular, to a stirred solution of hydrazine monohydrate (2.43 ml, 50 mmol) was slowly added γ-butyrothiolactone (0.43 ml, 5 mmol). After 4 hours the excess hydrazine was removed in vacuo. The crude product was purified by flash chromatography (SiO$_2$, 1:19 MeOH/MeCN) to give the desired product as a colorless oil. Yield: 599 mg (89%): $^1$H NMR (250 MHz, CDCl$_3$) δ 7.56 (s, 1 H), 3.89 (s, 2 H), 2.56-2.47 (q, J=6.9 Hz, 2 H), 2.28-2.22 (t, J=7.0 Hz, 2H), 1.94-1.83 (p, J=7.0 Hz, 2 H), 1.35-1.29 (t, J=8.0 Hz, 1 H); $^{13}$C NMR (62.9 MHz, CDCl$_3$) δ 173.02, 32.38, 29.16, 23.94; ESI-HRMS m/z 135.05955 (M+H$^+$, C$_4$H$_{11}$N$_2$OS calc'd 135.05921).

Example 2

Synthesis of Mercaptobutyric Acid Carbohydrazide (MBCH)

In another particular working embodiment, a carbohydrazide thiol linker was prepared from γ-butyrothiolactone according to Scheme 9.

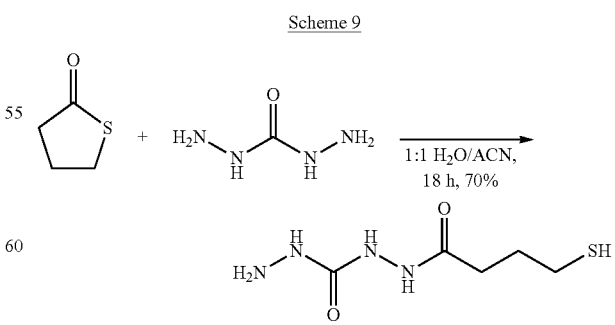

In particular, γ-butyrothiolactone (0.43 ml, 5 mmol) was diluted in acetonitrile (5 ml) and then slowly added to a solution of carbohydrazide (2.25 g, 25 mmol) in deionized water (5 ml). The reaction was stirred at 40° C. for 18 h, and then concentrated in vacuo. The crude product was removed by filtration and flash chromatography (SiO$_2$, 1:19 MeCN/MeOH) to give the product as a white solid. Yield: 672 mg (70%): $^1$H NMR (250 MHz, D$_2$O) δ 2.62-2.56 (t, J=7.1 Hz, 2 H), 2.47-2.41 (t, J=7.4 Hz, 2 H), 1.98-1.87 (m, 2 H); $^{13}$C NMR (62.9 MHz, D$_2$O) δ 179.14, 163.94, 34.86, 31.74, 25.91; ESI-HRMS m/z 215.05818 (M+Na$^+$, C$_5$H$_{12}$N$_4$NaO$_2$S calc'd 215.25787).

Example 3

Synthesis of Mercapto-dPEG$_4$-hydrazide

In yet another particular working embodiment, a PEG-based hydrazide thiol linker was prepared according to Scheme 10 to provide a mercapto-dPEG hydrazide.

Scheme 10

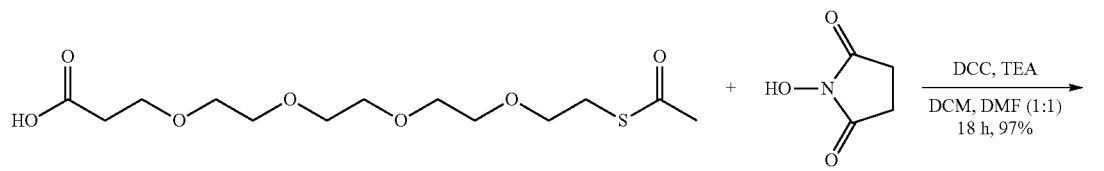

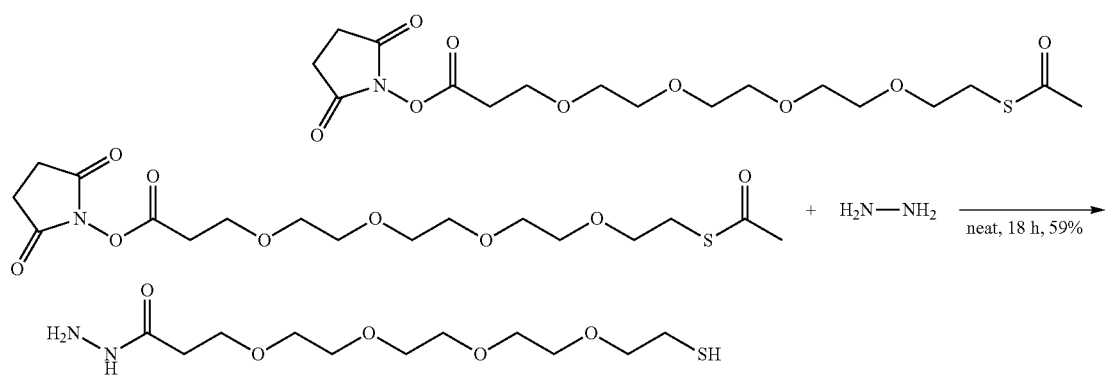

Acetyl-S-dPEG$_4$™-NHS ester (Quanta Biodesign, Powell, Ohio; 580 mg, 1.38 mmol) was slowly added to anhydrous hydrazine (10 ml), and was stirred for 18 h at ambient temperature. The reaction was concentrated in vacuo to give the crude product. Flash chromatography (SiO$_2$, 199:1 MeCN/AcOH) gave the product as a colorless oil. Yield: 240 mg (59%): $^1$H NMR (250 MHz, CDCl$_3$) δ 8.04 (s, 1 H), 3.88 (s, 2 H), 3.68-3.52 (m, 17 H), 2.65-2.60 (t, J=6.3 Hz, 2 H), 2.43-2.39 (t, J=5.8 Hz, 2H); $^{13}$C NMR (62.9 MHz, CDCl$_3$) δ 171.94, 72.74, 70.52, 70.49, 70.38, 70.15, 70.09, 66.72, 35.17, 24.12; ESI-HRMS m/z 319.13073 (M+Na$^+$, C$_{11}$H$_{24}$N$_2$NaO$_5$S calc'd 319.13036). An acetyl-S-dPEG$_8$™-NHS ester also is commercially available from Quanta Biodesign, (Powell, Ohio). In general, a mercapto-dPEG-hydrazide can have the formula H$_2$N—NH—CO—(CH$_2$—CH$_2$—O)$_t$—CH$_2$—CH$_2$—SH, where t=2 to 50.

Example 4

Synthesis of Conjugates of IgG and Alkaline Phosphatase

An Fc-specifically thiolated immunoglobulin was prepared according to Scheme 11.

Scheme 11

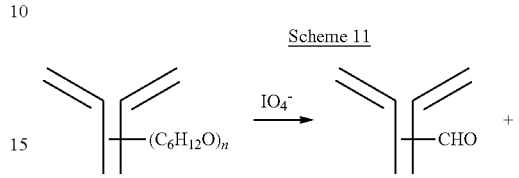

-continued

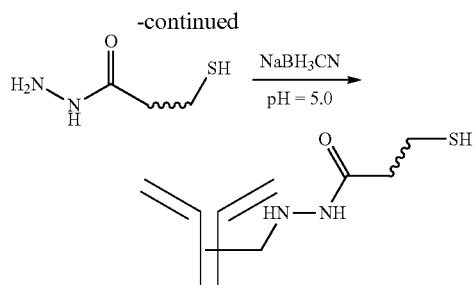

Specifically, to a solution of polyclonal antibody (1.5 ml, 3.0 mg/ml) was added sodium periodate (0.5 ml, 10 mg/ml in deionized water) for a final periodate concentration of 11.7 mM. The reaction solution was rotated for 2 hours before being passed through a PD-10 desalting column (0.1 M NaOAc, 1 mM EDTA, pH=5.0) to remove excess periodate. A hydrazide thiol linker (MBH, AMBH, MBCH or Mercapto-dPEG$_4$-hydrazide) was added in a 1000-fold molar excess to the antibody followed by sodium cyanoborohydride (3.14 mg, 50 μmol), and the reaction was rotated for a period of 18 h before being concentrated to a final volume of 1 ml. Size exclusion chromatography (Superdex 200; 0.1 M NaOAc, pH=5.0) gave the purified thiolated antibody. The number of thiols was quantitated through a modified Ellman's assay (see, for example, Hermanson, "Bioconjugate Techniques," Academic Press, San Diego, 1996, ISBN 0-12-342336-8, which is incorporated by reference herein). This procedure yielded an average of 3-5 thiol groups per antibody.

Reaction of a hydrazide thiol linker with an aldehyde group introduced to the Fc region of an immunoglobulin is advantageously performed at a mildly acidic pH, for example, a pH between 4 and 6 such as a pH near 5. Without wishing to be bound by theory, it is likely that at such mildly acidic pHs the aldehyde group is electrophilically activated by protonation of the aldehyde oxygen and, concurrently, the hydrazide group (pKa of about 4) is not substantially protonated and remains highly nucleophilic, thereby facilitating the reaction between the aldehyde group and the hydrazide group. Since such mildly acidic conditions also represent conditions where the sulfur of the thiol group is substantially protonated (substantially present in its neutral acid form) and thus unable to react with disulfides linking the heavy and light chains of an immunoglobulin, the reaction is facile and yet less likely to disrupt immunoglobulin structure. Furthermore, a free thiol group is maintained for further reaction to form a conjugate.

Thiol-reactive maleimide groups were introduced to alkaline phosphatase according to Scheme 12.

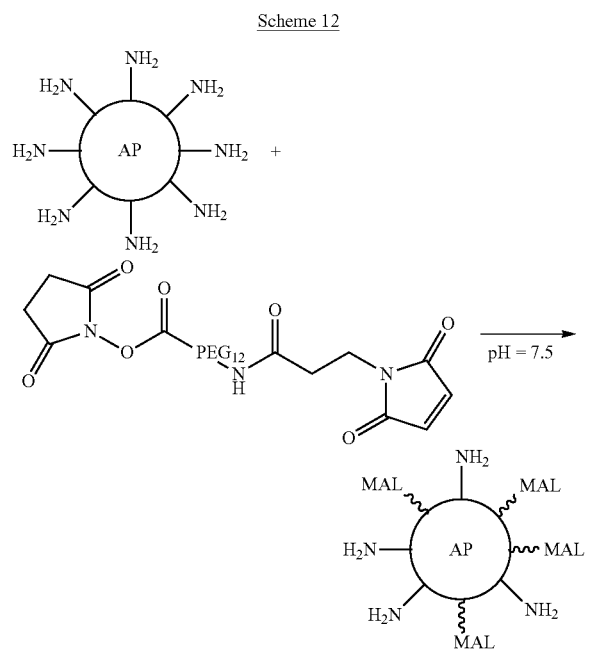

Specifically, alkaline phosphatase (Biozyme, San Diego, Calif.), which was received in a reactive buffer containing Tris, was passed through a PD-10 column in order to exchange the AP into a non-reactive buffer (0.1 M sodium phosphate, 0.1 M sodium chloride, 1 mM magnesium chloride, 0.1 mM zinc chloride, pH=7.5). Then, to a solution of alkaline phosphatase (0.8 ml, 17.5 mg/ml) a 100-fold excess of NHS-dPEG$_{12}$-MAL (Quanta Biodesign, Powell, Ohio) was added and the reaction was rotated for a period of 1 h.

Size exclusion chromatography (Superdex 200; 0.1 M Tris, 1 mM MgCl$_2$, 0.1 mM ZnCl$_2$, pH=7.5) yielded the purified maleimido-alkaline phosphatase. The number of maleimides was quantitated using a modified Ellman's assay (see, for example, Hermanson, "Bioconjugate Techniques," Academic Press, San Diego, 1996, ISBN 0-12-342336-8, which is incorporated by reference herein), and on average 17-25 maleimide groups were introduced to each alkaline phosphatase enzyme.

The final conjugation of the thiolated Ab and the reactive AP was then performed at a pH above 7, which in this instance allowed for fast formation of a conjugate by reaction of the thiol on the Ab (present to a greater extent in the conjugate base thiolate form at higher pHs) and the thiol-reactive maleimide group introduced to alkaline phosphatase. Scheme 10 below depicts the final conjugation of the thiolated Ab and the thiol-reactive AP.

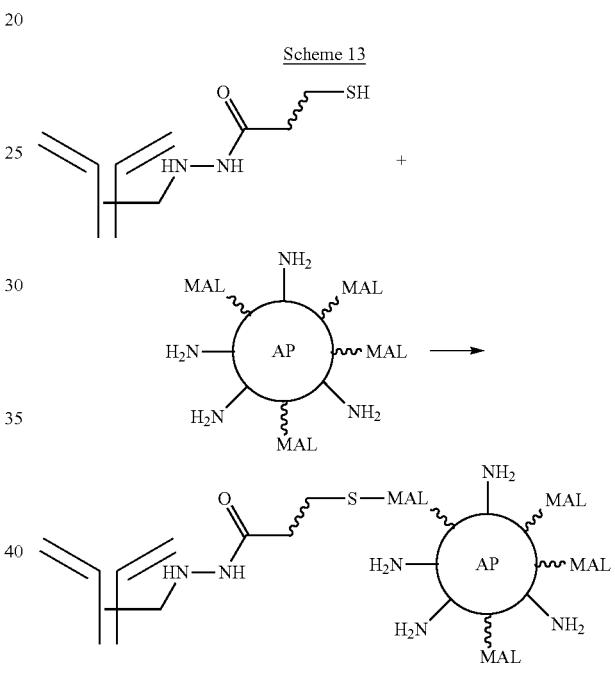

Specifically, the purified maleimido-alkaline phosphatase was combined with the purified thiolated antibody in a 1:1 molar ratio and rotated for a period of 18 h. Size exclusion chromatography (Superdex 200; 0.1 M Tris, 1 mM MgCl$_2$, 0.1 mM ZnCl$_2$, pH=7.5) gave the purified conjugate which was diluted to an $A_{280}$=0.0087 into a 1:1 dilution of Stabilzyme™ AP enzyme-stabilizing diluent (SurModics, Eden Prairie, Minn.) and analyzed on tissue as described in the examples that follow. The resulting conjugates showed unprecedented staining sensitivities in a variety of tissues, as shown in the Examples that follow.

The synthesis of the Ab-AP conjugate according to this procedure produces a 1:1 conjugate having a median molecular weight of approximately 270 kDa. This is true regardless of the antibody used to prepare the conjugate (such as goat anti-mouse IgG, goat anti-rabbit IgG and rabbit anti-DNP antibodies). The crude chromatograms, obtained after conjugation show overlap between product and starting material (median molecular weight of 145 kDa), which can be taken into consideration during the purification process.

Example 5

Detection of Kappa in Tonsil Tissue

In this example, the performance of an Ab-AP conjugate prepared using MBH according to the procedure of Example 4 was evaluated for its detection sensitivity in an in-situ hybridization (ISH) assay. The procedure utilized was adapted from a standard ISH protocol available on a BenchMark® automated slide staining instrument (Ventana Medical Systems, Inc., Tucson, Ariz.). The automated staining protocol was as follows.

A paraffin-embedded tonsil tissue sample on a slide was heated to 75° C. for 4 minutes and treated twice with EZPrep™volume adjust (Ventana Medical Systems, Inc., Tucson, Ariz.) at 75° C. before application of LiquidCoverslip™ (Ventana Medical Systems, Inc., Tucson, Ariz.) with EZPrep™ volume adjust. After 4 minutes at 75° C., the slide was rinsed and EZPrep™ volume adjust was added along with LiquidCoverslip™ to de-paraffinize the tissue at 76° C. for 4 minutes. Liquid coverslip was dispensed to cover the EZ-Prep. The slide was then heated to 90° C. for 4 minutes and rinsed before cooling to 37° C. ISH-Protease 1 (100 µl, Ventana Medical Systems, Inc., Tucson, Ariz.) was added, incubated for 2 minutes, and then rinsed, followed by the addition of a fluorescein-labeled kappa nucleic acid probe (100 µl, INFORM® Kappa, Ventana Medical Systems, Inc., Tucson, Ariz.). After a 4 minute incubation, the slide was heated to 85° C. for 12 minutes, then cooled to 47° C. and incubated for a further 64 minutes. The slide was rinsed four times before the addition of a mouse anti-fluorescein primary antibody (100 µl, Ventana Medical Systems, Inc., Tucson, Ariz.), which was incubated for 20 minutes, and then rinsed twice. At this point either a secondary antibody (for further amplification) was automatically added or the Ab-AP conjugate was manually added or added automatically from a dispenser. For the slides that were amplified, a rabbit anti-mouse antibody (100 µl, Ventana Medical Systems, Inc., Tucson, Ariz.) was added, incubated for 8 minutes and then the slide was rinsed twice. In either case, once the AP-Ab conjugate (goat anti-rabbit or rabbit anti-mouse IgG conjugate, for samples with and without the secondary antibody, respectively; 100 µl) was applied to the slide, the slide was incubated for 16 minutes and the slide was rinsed twice. Application of iView™ Blue Enhance enhancer (100 µl, Ventana Medical Systems, Inc., Tucson, Ariz.) was followed by incubation for 4 minutes and application of both iView™ Blue NBT (100 µl, Ventana Medical Systems, Inc., Tucson, Ariz.) and iView™ Blue BCIP (100 µl, Ventana Medical Systems, Inc., Tucson, Ariz.). BCIP, which is a substrate of alkaline phosphatase generates an insoluble dark blue/purple precipitate, and NBT enhances the color of the BCIP. The slide was then incubated for a period of 32 minutes, rinsed twice, and Counterstain NFR (100 µl, Ventana Medical Systems, Inc., Tucson, Ariz.) was added. After incubation with the counterstain for 6 minutes, the slide was again rinsed and taken off of the instrument. The slide was treated with a detergent wash before dehydration with the series ethanol, acetone then xylene. A coverslip was added to the slide and the slide was viewed and photographed through a microscope. A negative control slide that was not treated with the kappa probe also was prepared in a similar fashion.

For comparison, a reference tonsil tissue sample was stained using a similar procedure employing a SA-AP conjugate for detection of the kappa probe (the procedure included addition of the secondary antibody as above followed by extra amplification steps, wherein automated addition of a biotinylated anti-IgG antibody was performed instead of application of the Ab-AP conjugate, which was then followed by addition of the SA-AP conjugate) The use of biotin-labeled antibodies and SA-AP conjugates is an industry standard for detection in automated ISH staining methods and served as a reference on which to determine the relative performance of the Ab-AP conjugate. A negative control slide that was not treated with the kappa probe also was prepared in a similar fashion using SA-AP detection. Coverslips were added to the slides and the slides were viewed and photographed at 40× through a brightfield microscope.

FIG. 1 is a set of photomicrographs comparing the desired staining and background staining observed for kappa ISH detection in tonsil tissue using the antibody-alkaline phosphatase conjugate and the SA-AP conjugate. In FIG. 1A the staining of kappa without amplification afforded by the secondary antibody and using the disclosed antibody conjugate is shown. FIG. 1B shows a negative control slide treated with the conjugate. FIG. 1C shows the staining of kappa using the SA-AP, and FIG. 1D shows the negative control for the same. A comparison of FIGS. 1A and 1C demonstrates more defined staining by the antibody conjugate (even though fewer amplification steps were used), and a comparison of FIGS. 1B and 1D demonstrates the lower background provided by the antibody conjugate. These results illustrate the superiority of the non-biotin detection scheme enabled by the antibody conjugate.

Example 6

Detection of Lambda in Tonsil Tissue

The automated staining process described in Example 5 (with the exceptions that the fluorescein-labeled nucleic acid probe used was specific for Lambda; INFORM® Lamdba, Ventana Medical Systems, Inc., Tucson, Ariz.; and ISH Protease 1 was incubated for 4 minutes) was used to assess the performance of an Ab-AP conjugate for detection of Lambda in tonsil tissue. The Ab-AP conjugate was used without a secondary antibody amplification step and was prepared using MBH as described in Example 4. For comparison, a reference slide was prepared using the SA-AP conjugate detection scheme described in Example 4.

The results are presented in FIG. 2. Specifically, FIGS. 2A and 2B show the staining pattern obtained using the Ab-AP conjugate with and without (negative control) the addition of the Lambda specific nucleic acid probe, respectively. FIGS. 2C and 2D show the staining pattern obtained using the SA-AP conjugate with and without (negative control) addition of the Lambda probe, respectively. A comparison of FIGS. 2A and 2C shows that the staining pattern obtained using the Ab-AP conjugate is at least as intense as that seen with the SA-AP conjugate, despite the process used for the Ab-AP conjugate involving one less amplification step. A comparison of FIGS. 2B and 2D demonstrates that there is much less background staining (evidenced by darker overall staining of the tissue) by the Ab-AP conjugate. Again, these results demonstrate the advantageous reduction of background seen when the disclosed Ab-AP conjugate is employed.

Example 7

Detection of CMV in Lung Tissue

The automated staining process described in Example 5 (with the exceptions that the fluorescein-labeled nucleic acid probe used was specific for CMV; INFORM® CMV, Ventana Medical Systems, Inc., Tucson, Ariz.; and ISH Protease 1 was incubated for 4 minutes) was used to assess the performance of an Ab-AP conjugate for detection of CMV in lung tissue. The Ab-AP conjugate was used without a secondary antibody amplification step and was prepared using MBH as described in Example 4. For comparison, a reference slide was prepared using the SA-AP conjugate detection scheme described in Example 4.

The results are presented in FIG. 3. Specifically, FIG. 3A shows the staining pattern obtained using the Ab-AP conjugate in the presence of the probe, FIG. 3B shows the staining pattern obtained using the Ab-AP conjugate in the absence of the probe, FIG. 3C shows the staining pattern obtained using the SA-AP conjugate in the presence of the probe, and FIG. 3D shows the staining pattern using the SA-AP conjugated in the absence of the probe. A comparison of FIG. 3A and 3C shows that staining with the Ab-AP conjugate is more defined than and at least as intense (despite having one less amplification step) as the staining provided by the SA-AP conjugate. Furthermore, less background staining is seen for the Ab-AP conjugate. The reduction in background provided by the Ab-AP conjugate also is evident from a comparison of FIGS. 3B and 3D.

Example 8

Detection of EBER in Spleen Tissue

The automated staining process described in Example 5 (with the exceptions that the fluorescein-labeled nucleic acid probe used was specific for EBER; INFORM® EBER, Ventana Medical Systems, Inc., Tucson, Ariz.; and ISH Protease 1 was incubated for 4 minutes) was used to assess the performance of an Ab-AP conjugate for detection of EBER in spleen tissue. The Ab-AP conjugate was used without a secondary antibody amplification step and was prepared using MBH as described in Example 4. For comparison, a reference slide was prepared using the SA-AP conjugate detection scheme described in Example 4.

The results are presented in FIG. 4. Specifically, FIG. 4A shows the staining pattern obtained using the Ab-AP conjugate in the presence of the probe, FIG. 4B shows the staining pattern obtained using the Ab-AP conjugate in the absence of the probe, FIG. 4C shows the staining pattern obtained using the SA-AP conjugate in the presence of the probe, and FIG. 4D shows the staining pattern using the SA-AP conjugated in the absence of the probe. A comparison of FIG. 4A and 4C shows that staining with the Ab-AP conjugate is more defined than and at least as intense (despite having one less amplification step) as the staining provided by the SA-AP conjugate. Furthermore, less background staining is seen for the Ab-AP conjugate. The reduction in background provided by the Ab-AP conjugate also is evident from a comparison of FIGS. 3B and 3D

Example 9

Detection of HPV in Tissue Xenografts

In this example, the performance of an Ab-AP conjugate that was prepared using MBH according to the procedure of Example 4 was assessed, in part, to determine if it provided enough sensitivity to permit a further reduction in the number of steps needed to detect HPV sequences by ISH. The results show that it is possible to achieve a reduction in the number of steps needed for detection, thereby making the disclosed Ab-AP conjugate very useful for an automated process where a reduction in the number of steps leads to a significant reduction in processing time and concomitantly, assay cost.

The three detection schemes presented below as Schemes 14-16, were performed in an automated or semi-automated fashion. In each of these schemes, a DNP-labeled nucleic acid probe that specifically binds to at least a portion of an HPV nucleic acid sequence is first added to the sample. The subsequent steps depicted in these schemes are steps used to detect the presence of the probe bound to HPV nucleic acid.

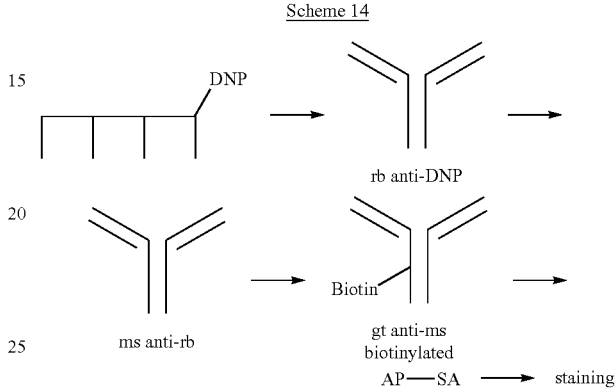

In Scheme 14, an anti-DNP antibody is first bound to the probe. An anti-IgG antibody is then added (first amplification step). In a second amplification step, a biotinylated anti-IgG antibody is added. An SA-AP conjugate is added, which binds to the biotinylated antibody, and staining is accomplished through addition of a chromogenic substrate that is acted upon by AP. In scheme 15, the second amplification step is eliminated, and an anti-IgG antibody conjugated to AP is added prior to staining rather than an SA-AP conjugate. In scheme 16, both amplification steps are eliminated and the DNP-labeled probe is directly detected by an anti-DNP antibody conjugated to AP.

HPV detection in a variety of cell lines grown in xenografts in SCID mice was performed according to the following procedure adapted from a standard ISH protocol for the BenchMark® automated staining instrument (Ventana Medical Systems, Inc, Tucson, Ariz.). Paraffin-embedded tissue on a slide was heated to 75° C. for 4 minutes and then treated twice with EZPrep™ volume adjust (Ventana Medical Systems, Inc., Tucson, Ariz.) at 75° C. before application of Liquid Coverslip™ (Ventana Medical Systems, Inc., Tucson, Ariz.) with EZPrep™ volume adjust. After 4 minutes at 75° C., the slide was rinsed and EZPrep™ volume adjust was added to de-paraffinize the tissue at 76° C. for 4 minutes. Liquid Coverslip was dispensed to cover the EZPrep™. Cell Conditioner #2, cell conditioning solution (Ventana Medical Systems, Inc., Tucson, Ariz.) was added, the slide warmed to 90° C., and incubated for 8 minutes. This was followed by another application of Cell Conditioner #2 and yet another incubation at 90° C. for 12 minutes. The slide was rinsed with Reaction Buffer (Ventana Medical Systems, Inc., Tucson, Ariz.), cooled to 37° C. and ISH-Protease 3 (100 µl, Ventana Medical Systems, Inc., Tucson, Ariz.) was added. After an incubation of 4 minutes, the slide was rinsed three times before the application of a hybridization buffer (iView™ Plus HybReady™ Solution, 100 µl, Ventana Medical Systems, Inc., Tucson, Ariz.) and was incubated for 4 minutes. Addition of a DNP-labeled HPV nucleic acid probe (HPV HR Probe, 200 µl, Ventana Medical Systems, Inc., Tucson, Ariz.) was followed by an incubation of 4 minutes at 37° C., 12 minutes at 95° C. and 124 minutes at 52° C. The slide was then rinsed twice and warmed to 72° C. This last step was repeated two more times before cooling the slide down to 37° C., and then, depending upon the detection scheme followed, such slides were treated in an automated or semi-automated fashion in one of three ways.

In one instance, as depicted in Scheme 14, an iView™+ Anti-DNP (100 µl, Ventana Medical Systems, Inc, Tucson, Ariz.) primary antibody was applied, and incubated for 20 minutes. The slide was then rinsed twice before the addition of the iView™+Amp (100 µl, Ventana Medical Systems, Inc, Tucson, Ariz.) secondary antibody. Incubation of the conjugate occurred for 8 minutes before rinsing the slide. The addition of iVIEW™+Biotin-Ig (100 µl, Ventana Medical Systems, Inc, Tucson, Ariz.) was followed by a 12 minute incubation and addition of the iVIEW™+SA-AP (100 µl, Ventana Medical Systems, Inc, Tucson, Ariz.). The slide was rinsed three times before the application of the iView™+ Enhancer (100 µl VMSI) which was followed by incubation for 4 minutes and application of both iView™+NBT (100 µl, Ventana Medical Systems, Inc, Tucson, Ariz.) and iView™+ BCIP (100 µl, Ventana Medical Systems, Inc, Tucson, Ariz.). The slide was then incubated for a period of 24 minutes, rinsed three times, and Counterstain NFR (100 µl, Ventana Medical Systems, Inc, Tucson, Ariz.) was added. After incubation with the counterstain for 4 minutes, and slide was rinsed three more times and taken off of the instrument. The slide was treated with detergent wash before dehydration with a series of ethanol, acetone and then xylene. A coverslip was applied to the slide and then the slide was viewed and photographed through a brightfield microscope.

In another instance, as depicted in Scheme 15, a rabbit anti-DNP primary antibody was added (iView™ Plus anti-DNP primary antibody, 100 µl, Ventana Medical Systems, Inc., Tucson, Ariz.). The primary antibody was incubated for 20 minutes and the slide was then rinsed twice before the manual addition (this step can also be automated to make the procedure fully automated) of the anti-rabbit IgG antibody conjugated to alkaline phosphatase (100 µl). Incubation of the conjugate occurred for 16 minutes before rinsing the slide four times. Application of the iView™ Plus Enhancer (100 µl, Ventana Medical Systems, Inc., Tucson, Ariz.) was followed by incubation for 4 minutes and application of both NBT and BCIP for color development (iView™ Plus NBT and iView™ Plus BCIP, 100 µl, Ventana Medical Systems, Inc., Tucson, Ariz.). The slide was then incubated for a period of 24 minutes, rinsed three times, and Counterstain NFR (100 µl, Ventana Medical Systems, Inc., Tucson, Ariz.) was added. After incubation with the counterstain for 4 minutes, and slide was rinsed three more times and taken off of the instrument. The slide was treated with a detergent wash before dehydration with ethanol, acetone and xylene. Following application of a cover slip, the slide was viewed through a microscope and photographed at 40× using a brightfield microscope.

In yet another instance, as depicted in scheme 16, the slide was treated directly with an alkaline phosphatase rabbit anti-DNP conjugate (100 µl). The slide was incubated for 20 minutes and was then rinsed twice before the application of the iView™+Enhancer (100 µl, Ventana Medical Systems, Inc, Tucson, Ariz.). This was followed by incubation for 4 minutes and simultaneous application of both iView™+NBT (100 µl, Ventana Medical Systems, Inc, Tucson, Ariz.) and iView™+BCIP (100 µl, Ventana Medical Systems, Inc, Tucson, Ariz.). The slide was then incubated for a period of 24 minutes, rinsed three times, and Counterstain NFR (100 µl, Ventana Medical Systems, Inc, Tucson, Ariz.) was added. After incubation with the counterstain for 4 minutes, and slide was rinsed three more times and taken off of the instrument. The slide was treated to a detergent wash before serial dehydration with ethanol, acetone and xylene. A coverslip was added to slide and it was viewed and photographed at 40× using a brightfield microscope.

Figure 5A:
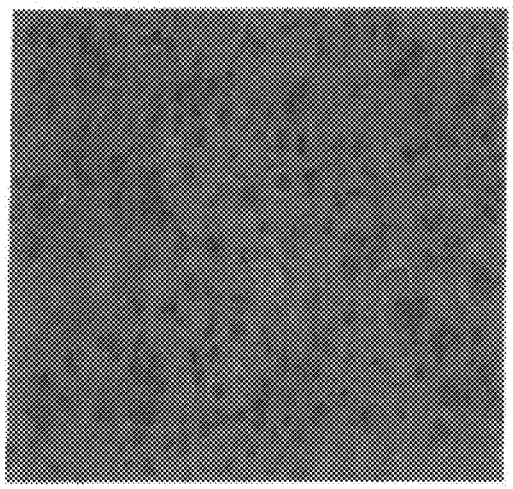
FIGS. 5A-5C are a series of images showing staining patterns for detection of HPV in CaSki xenograft tissue using a disclosed Fc-specific antibody-alkaline phosphatase conjugate and using a streptavidin-alkaline phosphatase conjugate.
Figure 5B:
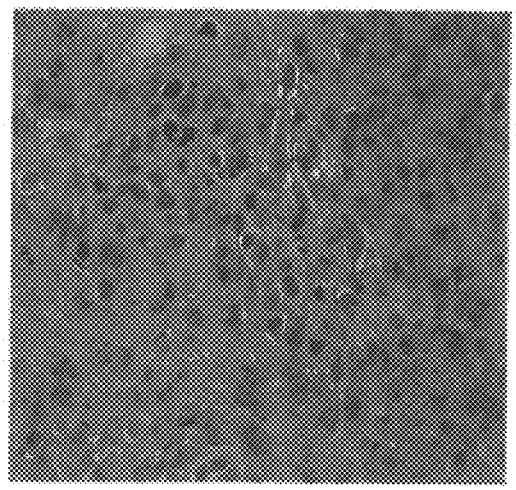
Figure 5C:
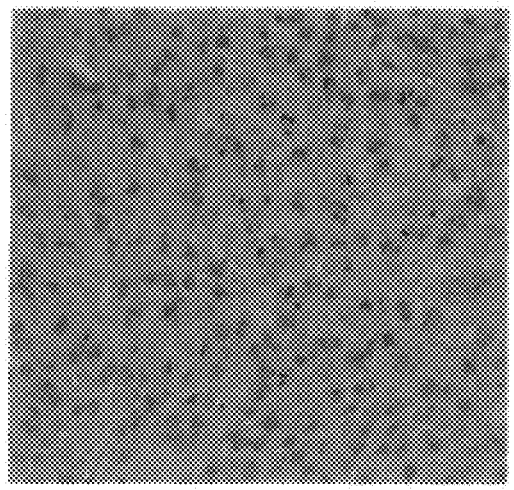
Figure 6A:
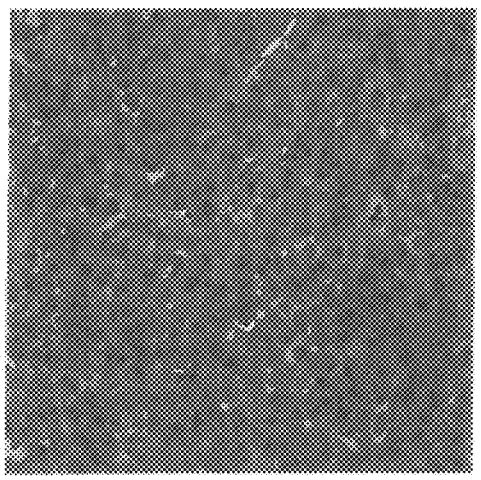
FIGS. 6A-6C are a series of images showing staining patterns for detection of HPV in HeLa xenograft tissue using a disclosed Fc-specific antibody-alkaline phosphatase conjugate and using a streptavidin-alkaline phosphatase conjugate.
Figure 6B:
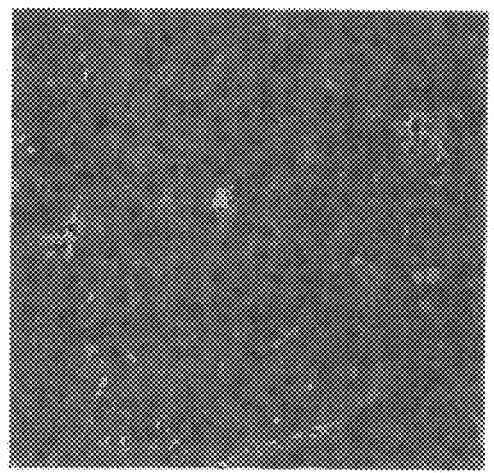
Figure 6C:
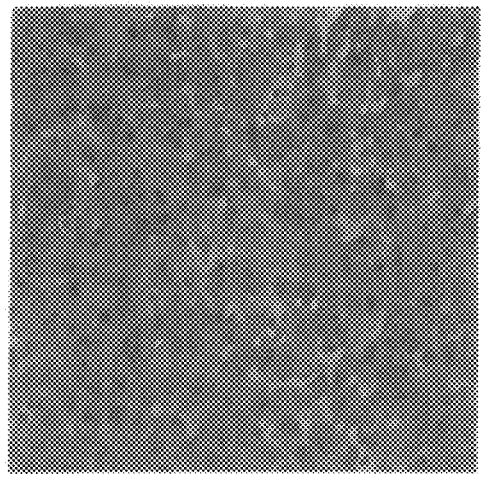
Figure 7A:
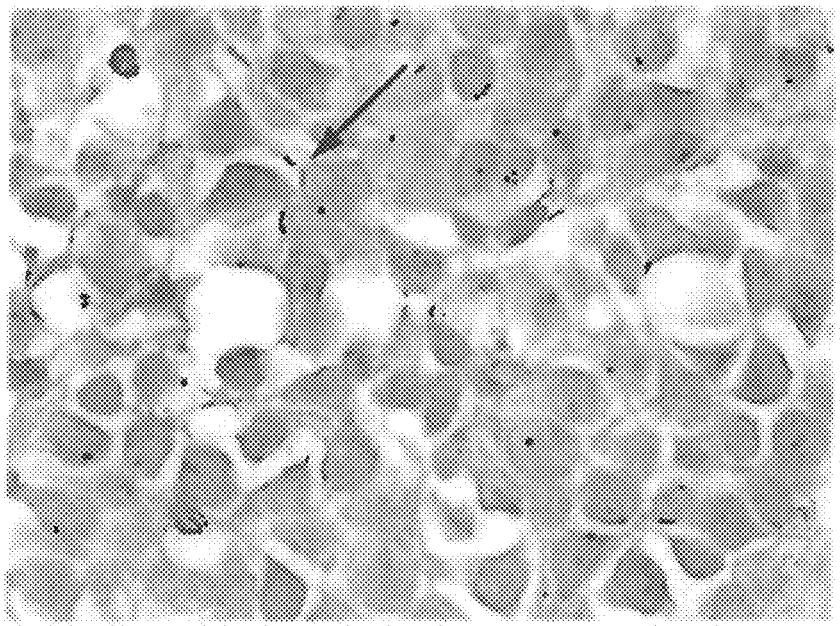
FIGS. 7A and 7B are images showing staining patterns for detection of HPV in SiHa xenograft tissue using a disclosed Fc-specific antibody-alkaline phosphatase conjugate and using a streptavidin-alkaline phosphatase conjugate.
Figure 7B:
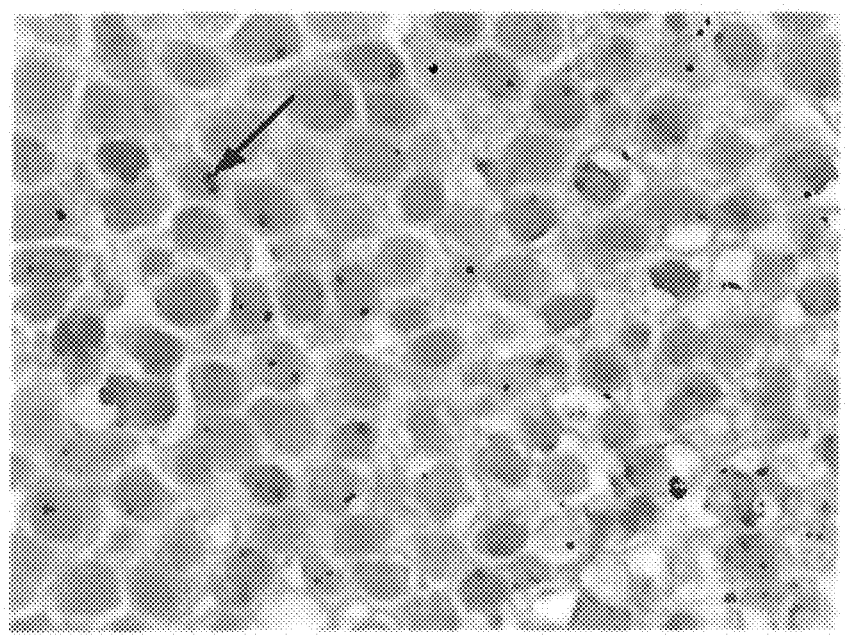

FIGS. 5-7 show the results of HPV detection in three different xenograft tissue types. In FIGS. 5A, 5B and 5C, the staining patterns for HPV detection in CaSki xenograft tissue according to each of Schemes 14, 15 and 16 are shown, respectively. In FIGS. 6A, 6B and 6C, the staining patterns for HPV detection in HeLa xenograft tissue according to each of Schemes 14, 15 and 16 are shown, respectively. In FIGS. 7A and 7B, the staining patterns for single copy HPV detection (indicated by arrows) in SiHa xenograft tissue according to each of Schemes 14 and 15 are shown, respectively.

A comparison of FIGS. 5A and 5B demonstrates that the staining intensity provided by detection according to Scheme 15 is greater than that provided according to Scheme 14 even though Scheme 15 includes two fewer amplification steps. FIG. 5C demonstrates that HPV detection can be accomplished without amplification using direct detection (Scheme 16) with an Ab-AP conjugate prepared according to Example 4. A comparison of FIGS. 6A and 6B also demonstrates that the staining intensity provided by detection according to Scheme 15 is greater than that provided according to Scheme 14, even though Scheme 15 includes two fewer steps of amplification. FIG. 6C demonstrates that HPV detection can be accomplished without amplification using direct detection (scheme 16) with an Ab-AP conjugate prepared according to Example 4. A comparison of FIGS. 7A and 7B shows that even single copies of HPV nucleic acid sequences can be detected with the detection process of Scheme 15. Overall, the results demonstrate that the superior sensitivity exhibited by a disclosed Fc-specific Ab-AP facilitates automated detection by reducing the number of steps needed to detect HPV in tissue samples. The reduction of the number of steps between Schemes 14 and 15 can reduce the total automated staining process time by 15% (from 6.5 hrs to 5.5 hrs). Further reductions in process time can be realized by use of Scheme 16.

While a DNP labeled probe and specific types of antibodies were described in this example, one of ordinary skill in the art will appreciate that many other haptens (such as fluorescein, digoxigenin and biotin) can be used to label nucleic acid sequences and that the use of multiple nucleic acid probes to different targets, each having a different hapten label, can be used to permit multiplexed detection (such as with different detection antibodies conjugated to different fluorescent nanoparticles that emit light of various different wavelengths). Furthermore, one of ordinary skill in the art will recognize that antibodies of other types and from other species than those described, other detectable labels, and other reagents for generating a detectable signal can be used in similar assays to detect other targets.

Example 10

Detection of HPV in Liquid-Based Preparations

Slides for the liquid-based prep HPV assay were prepared using the ThinPrep® 2000 System slide preparation system (Cytyc Corporation, Marlborough, Mass.). Cells obtained through vaginal scraping are placed within a methanol-based, buffered preservative solution (ThinPrep® PreservCyt Solution, Cytyc Corporation, Marlborough, Mass.) and then layered onto the glass slide by the instrument.

The following is an adapted procedure from the Ventana BenchMark® Instrument: the liquid based prep slide was heated to 65° C. for 12 minutes followed by an additional 4 minutes at 75° C. and rinsed twice with Reaction buffer (Ventana Medical Systems, Inc, Tucson, Ariz.; 1.2 ml) at 75° C. before application of the liquid cover slip (Ventana Medical Systems, Inc, Tucson, Ariz.). The slide was then rinsed with 0.9 ml of Rinse Buffer (Ventana Medical Systems, Inc, Tucson, Ariz.) followed by the application of Cell Conditioner #2 cell conditioning solution (Ventana Medical Systems, Inc, Tucson, Ariz.) and the slide was warmed to 90° C. and incubated for 16 minutes. The slide was rinsed with Reaction Buffer, cooled to 37° C. and ISH-Protease 3 (100 µl, Ventana Medical Systems, Inc, Tucson, Ariz.) was added. After an incubation of 4 minutes, the slide was rinsed three times before the application of iView™+HybReady (100 µl, Ventana Medical Systems, Inc, Tucson, Ariz.) which was incubated for 4 minutes. Addition of HPV HR Probe (200 µl, Ventana Medical Systems, Inc, Tucson, Ariz.) was followed by an incubation of 4 minutes at 37° C., 12 minutes at 95° C. and 124 minutes at 52° C. The slide was then rinsed twice and warmed to 72° C. This last step was repeated two more times before cooling the slide down to 37° C. and adding iView™+Anti-DNP (100 µl, Ventana Medical Systems, Inc, Tucson, Ariz.).

For standard SA-AP detection (according to Scheme 14 above), the primary antibody was incubated for 20 minutes and the slide was then rinsed twice before the addition of the i™VIEW+Amp secondary antibody (Ventana Medical Systems, Inc, Tucson, Ariz., 100 µl). Incubation of the antibody occurred for 8 minutes before rinsing. Then, the i™VIEW+Biotin-IgG antibody conjugate (Ventana Medical Systems, Inc, Tucson, Ariz., 100 µl) was added followed by a 12 minute incubation and rinse step. Lastly, the iVIEW™+SA-AP conjugate (Ventana Medical Systems, Inc, Tucson, Ariz., 100 µl) was added and after an 8 minute incubation, the slide was rinsed three times with Reaction Buffer. For detection using the Ab-AP conjugate as the secondary antibody (according to Scheme 15 above), the primary antibody was incubated for 20 minutes and the slide was then rinsed twice before the addition of the AP-IgG conjugate (100 µl). Incubation of the conjugate occurred for 8 minutes before rinsing three times with Reaction Buffer. For direct detection of the labeled probe using the Ab-AP conjugate, the conjugate was incubated for 20 minutes before the slide was rinsed three times with Reaction Buffer.

In all three cases, the steps above were followed by application of iVIEW+Enhancer (100 µl, Ventana Medical Systems, Inc, Tucson, Ariz.) was followed by incubation for 4 minutes and application of both iVIEW™+NBT (100 µl, Ventana Medical Systems, Inc, Tucson, Ariz.) and iVIEW™+BCIP (100 µl, Ventana Medical Systems, Inc, Tucson, Ariz.). The slide was then incubated for a period of 24 minutes, rinsed three times, and Counterstain NFR (100 µl, Ventana Medical Systems, Inc, Tucson, Ariz.) was added. After incubation with the counterstain for 4 minutes, and slide was rinsed three more times and taken off of the instrument. The slide was treated with a detergent wash before dehydration with ethanol, acetone and xylene and subsequent application of a cover slip to the slide, after which the slide was viewed through a microscope.

Figure 8A:
FIGS. 8A-8C are a series of images showing staining patterns for detection of HPV in cytology samples using a disclosed Fc-specific antibody-alkaline phosphatase conjugate and using a streptavidin-alkaline phosphatase conjugate.
Figure 8B:
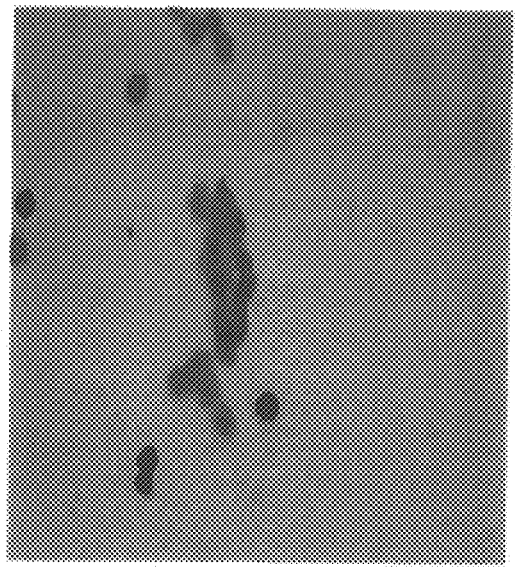
Figure 8C:
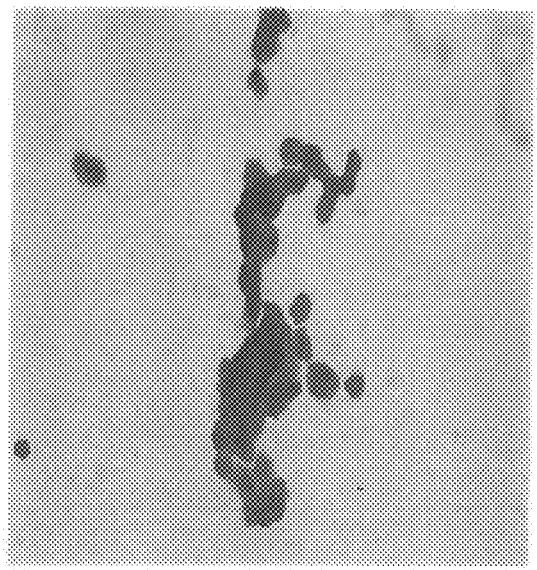

A comparison of FIGS. 8A and 8B shows that detection according to Scheme 15 (see, Example 9), using an Ab-AP conjugate that was prepared using MBH according to the procedure of Example 4, provides more intense staining than provided by detection using an SA-AP conjugate according to Scheme 14 (see, Example 9). A comparison of FIGS. 8B and 8C demonstrates that direct detection using an anti-DNP Ab-AP conjugate according to Scheme 16 (see, Example 9) provides a signal that is comparable to the signal provide by an SA-AP conjugate according to Scheme 14. These results again demonstrate that the detection sensitivity provided by an Fc-specific Ab-AP conjugate according to Example 4 permits a reduction in the number of steps needed to provide adequate signals, thereby facilitating automation.

Example 11

Detection of Actin in Muscle Tissue

In this example, immunohistochemical detection of a protein target (actin) using an Ab-AP conjugate prepared as described in Example 4 with an MBH linker was compared to the performance of a SA-AP conjugate.

The following is the adapted procedure from the Ventana BenchMark® Instrument: the paraffin coated tissue on the slide was heated to 75° C. for 4 minutes and treated twice with EZPrep™ volume adjust (Ventana Medical Systems, Inc, Tucson, Ariz.) at 75° C. before application of the liquid cover slip (Ventana Medical Systems, Inc, Tucson, Ariz.) with EZPrep™ volume adjust. After another 4 minutes at 76° C., the slide was rinsed and Depar volume adjust (Ventana Medical Systems, Inc, Tucson, Ariz.) was added along with liquid cover slip to de-paraffinize the tissue. The slide was then cooled to 42° C. for 2 minutes, before reaching the final temperature of 37° C. The primary antibody was then added (100 µl anti-muscle actin, Ventana Medical Systems, Inc, Tucson, Ariz.) and the slide incubated at 37° C. for 16 minutes. The slide was then rinsed twice and the alkaline phosphatase conjugated goat anti-mouse material (100 µl) was added and incubated 37° C. for 16 minutes. The slide was rinsed once before the simultaneous addition of Enhanced V-Red Enhancer (100 µl, Ventana Medical Systems, Inc, Tucson, Ariz.) and Enhance Naphthol (100 µl, Ventana Medical Systems, Inc, Tucson, Ariz.), and the slide was again incubated at 37° C. for 4 minutes. This was followed by the addition of Enhance Fast Red A (100 µl, Ventana Medical Systems, Inc, Tucson, Ariz.) an 8 minute incubation and the addition of Enhance Fast Red B (100 µl, Ventana Medical Systems, Inc, Tucson, Ariz.) with a final 8 minute incubation. After development of the stain, the slide was treated with a detergent wash before dehydration with ethanol, acetone and xylene and subsequent application of a cover slip to the slide, after which the slide was viewed through a microscope.

Figure 9A:
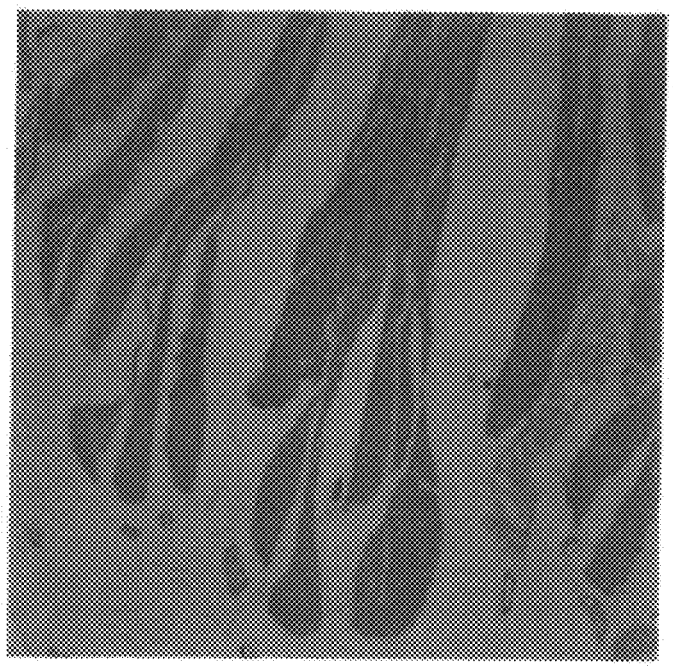
FIGS. 9A and 9B are images showing staining patterns for detection of actin in muscle tissue using a disclosed Fc-specific antibody-alkaline phosphatase conjugate and using a streptavidin-alkaline phosphatase conjugate.
Figure 9B:
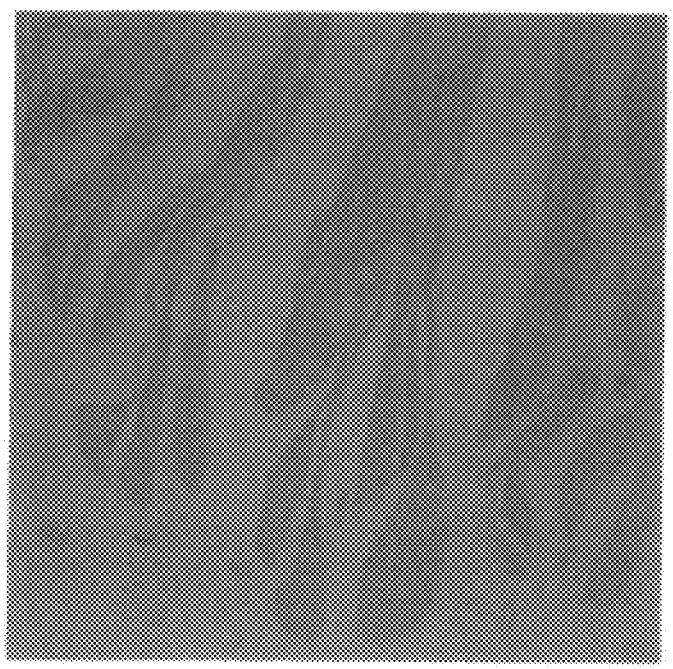
Figure 10A:
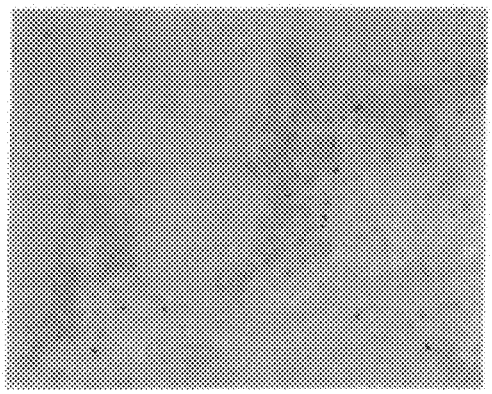
FIGS. 10A-10G are a series of images showing a comparison of the sensitivity of disclosed antibody-enzyme conjugates with each other and with antibody-body enzyme conjugates prepared by other methods.
Figure 10B:
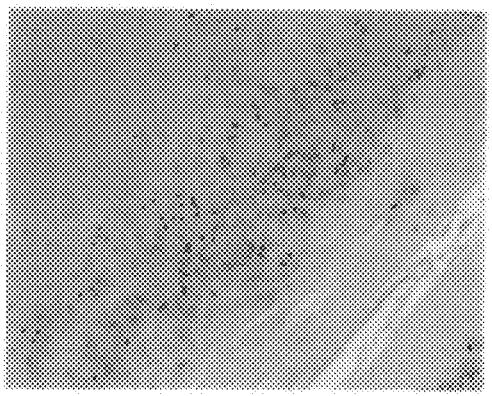
Figure 10C:
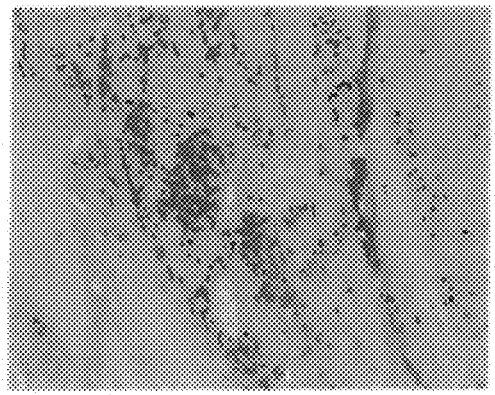
Figure 10D:
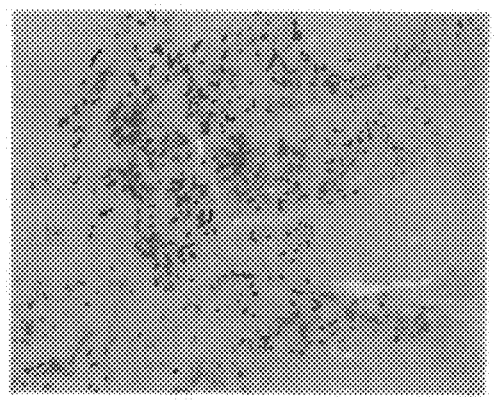
Figure 10E:
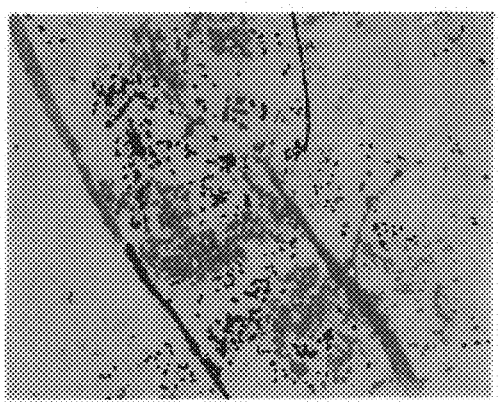
Figure 10F:
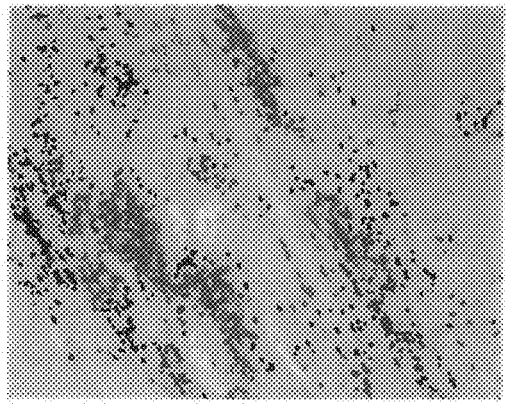
Figure 10G:
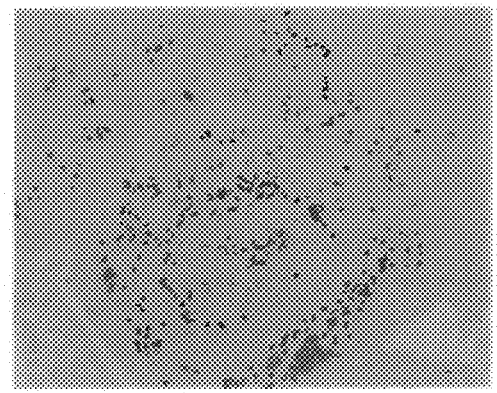

The results are presented in FIG. 9. Specifically, FIG. 9A shows that detection using the Ab-AP conjugate and a single amplification step is superior to detection using an SA-AP conjugate and two amplification steps (FIG. 9B). These results again demonstrate the superior detection sensitivity provided by Fc-specific antibody conjugates according to the disclosure.

Example 12

Variation of Antibody Linker Length and Type

In this example, the effect of linker length and type on conjugate composition and staining characteristics was determined. Several conjugates were prepared according to the method of Example 4, but using a variety of hydrazide thiol linkers, specifically, conjugates prepared using a thio-$PEG_4$-hydrazide linker, a mercaptobutyric acid hydrazide (MBH) linker, and a mercaptobutyric acid carbohydrazide (MBCH) linker. These conjugates were compared to each other and to a conjugate prepared through generation of thiols by reduction of immunoglobulin disulfides, specifically an Ab-AP conjugate prepared by the method described in co-pending U.S. Provisional Patent Application No. 60/675,759 that involves generation of thiols via DTT reduction followed by conjugations using a PEG-based maleimide-NHS bifunctional linker. Also for comparison, a commercially available acetamidomercaptobutyric acid hydrazide (AMBH, Invitrogen, Eugene, Oreg.) linker was used in the method of Example 4 to generate an Ab-AP conjugate. In addition, an Ab-AP conjugate prepared with a maleimido-hydrazide (EMCH; N[ε-Maleimidocaproic acid]hydrazide, Pierce Biotechnology, Rockford, Ill.) using the manufacturer's instructions was prepared and used in the staining protocol for comparison. Furthermore, the Fc-specific conjugation method described in U.S. Pat. No. 5,191,066 employing cystamine was used to provide Fc-specific Ab-AP conjugate for comparison.

Ellman's Assay results showed that between 3-5 thiols/Ab were added to an immunoglobulin through addition with the MBH and PEG-based hydrazide thiol linkers, 5-7 thiols/Ab for the AMBH and MBCH linkers, and 8-12 thiols/Ab for the DTT reduction method. After coupling of the thiols introduced or generated in the immunoglobulin to maleimide-derivatized AP, size exclusion chromatograms were obtained.

Size exclusion chromatograms were obtained using an AKTA Purifier LC (GE Biosciences, Uppsala, Sweden) using a Superdex 10/300 200 GL column and 0.1 M Tris, 1 mM $MgCl_2$, 0.1 mM $ZnCl_2$, pH=7.5 as the mobile phase. The flow rate was held at 1 ml/min in all cases. From the size exclusion chromatograms, it was determined that the best yield of conjugate was obtained using AMBH. However, it began to precipitate out of solution when stored at 2-8° C. for 48 hours. The other linkers all yielded conjugates having similar size exclusion profiles.

FIG. 10 compares the staining as outlined in Example 6 of Kappa on tonsil tissue using the conjugates as the secondary antibody. FIG. 10A shows the staining pattern seen for an Ab-AP conjugate prepared with EMCH. FIG. 10B shows the staining pattern seen for the Fc-specific cystamine method of U.S. Pat. No. 5,191,066. FIG. 10C shows the staining pattern seen for the Ab-AP conjugate prepared by a DTT reduction method according U.S. patent application Ser. No. 11/413,418, filed Apr. 27, 2006. that utilized a dPEG-based bifunctional linker FIG. 10D shows the staining pattern seen for the Ab-AP conjugated prepared with the commercially available AMBH linker using the disclosed method of Fc-specific conjugation. FIG. 10E shows the staining pattern seen for the Ab-AP conjugate prepared according to the disclosed Fc-specific conjugation method employing the disclosed MBH linker of Example 1. FIG. 10F shows the staining pattern seen for the Ab-AP conjugate prepared according to the disclosed Fc-specific conjugation method employing the disclosed $dPEG_4$ hydrazide thiol linker of Example 3. FIG. 10G shows the staining pattern seen for the Ab-AP conjugate prepared according to the disclosed Fc-specific conjugation method employing the disclosed MBCH hydrazide thiol linker of Example 2. A comparison of the staining patterns reveals the following trend for the staining intensity provided by the conjugates:

EMCH<Cystamine<AMBH<MBCH<PEG4=DTT<MBH

The images illustrate the superior sensitivity that can be achieved by Fc-specific conjugation of enzymes using the disclosed method and various disclosed and commercially available hydrazide thiol linkers. The disclosed method also yields superior conjugates to the cystamine Fc-specific method and coupling with EMCH. Only the DTT-mediated method of conjugation provides conjugates that give similar specificity and sensitivity.

Example 13

Variation of MBH Linker Excess

In this example, the dependence of conjugate composition and staining characteristics on the excess of hydrazide thiol linker was determined. Synthesis of AP-IgG conjugates with MBH linker was carried out following the procedure of Example 4, however the molar excess of the MBH linker was varied from a five thousand-fold excess to a fifty-fold excess. The results from the Ellman's Assay showed the following number of thiols/Ab: 5000×—9-15; 1000×—7-10; 500×—3-5; 100×—2-4; 50×—1-3. Analysis of the conjugates (5000×, 1000×, 500×, 100×, and 50×) after reaction with the maleimide-derivatized Ab was performed by size exclusion chromatography and showed that the conjugates synthesized using a larger excess of linker had a higher overall yield. However, the tissue staining (anti-mouse—muscle, muscle actin; anti-rabbit—skin, S100) for each of these conjugates showed that the 500× had the most intense stain with the lowest amount of background.

Example 14

Variation of Alkaline Phosphatase Linker Length/Type

In this example, the dependence of conjugate composition and staining characteristics on the length and type of linker used to add thiol-reactive groups to alkaline phosphatase was determined. Synthesis of AP-IgG conjugates with MBH linker was carried out following the procedure of Example 4, but the following linkers were used to activate alkaline phosphatase for reaction with the thiolated antibody: LC-SMCC (Pierce, Rockford, Ill.), MAL-dPEG$_8$-NHS ester (Quanta Biodesign, Powell, Ohio), MAL-dPEG$_4$-NHS ester (Quanta Biodesign, Powell, Ohio) and MAL-dPEG$_{12}$-NHS ester (Quanta Biodesign, Powell, Ohio). Each of these linkers was reacted with AP in a hundred-fold excess, in a buffer system (0.1 M sodium phosphate. 0.1 M NaCl, 1 mM MgCl$_2$, 0.1 mM ZnCl$_2$, pH=7.5) for 1 hour. The LC-SMCC had to be dissolved in dimethylformamide (DMF) and added to the AP, but not exceeding 10% total volume of DMF in buffer. Ellman's Assay showed a maleimide incorporation of 20/AP for the PEG$_{12}$ and LC-SMCC linkers, 27/AP for the PEG$_8$ linker and 30/AP for the PEG$_4$ linker. After coupling to an Fc-thiolated antibody (made with MBH), size exclusion chromatograms were obtained upon purification. The PEG$_{12}$ linker gave the highest conjugate yield, followed by the PEG$_8$, LC-SMCC, and the PEG$_4$ linkers. The tissue staining (anti-mouse—muscle, muscle actin; anti-rabbit—skin, S100) mirrored the conjugate yield with the PEG$_{12}$ conjugate giving the most intense staining.

Example 15

Variation of NHS-PEG$_{12}$-MAL Linker Excess

In this example, the dependence of conjugate composition and staining characteristics on excess of NHS-PEG$_{12}$-MAL linker used to add thiol-reactive groups to alkaline phosphatase was determined. Syntheses of an AP-IgG conjugates according to the method of Example 4 was performed where the molar excess of a MAL-dPEG$_{12}$-NHS ester linker was varied from a five hundred-fold excess to a twenty-five-fold excess.

Ellman's Assay results showed maleimide incorporation of: 500×—34 maleimides; 250×—29 maleimides; 100×—18-20 maleimides; 50×—17 maleimides; 25×—15 maleimides. Analysis of the conjugates (500×, 250×, 100×, 50×, and 25×), after reaction with the Fc-thiolated Ab, using size exclusion chromatography showed that the conjugates synthesized using a larger excess of linker had a larger yield and a higher percentage of maleimide incorporation. Tissue staining (anti-mouse—muscle, muscle actin; anti-rabbit—skin, S100) for each of the conjugates showed that use of 100× maleimide gave the sharpest, most intense staining.

Example 16

Variation of AP/Ab Molar Ratios

In this example, the dependence of conjugate composition and staining characteristics on the ratio of the thiolated antibody (prepared with an MBH-linker) to the maleimide-derivatized AP (NHS-PEG$_{12}$-MAL linker) in the final reaction was determined. The following ratios (Antibody/AP) were used: 2:1, 1:1, 1:2, and 1:3. The profiles of size exclusion chromatographs showed that maximum yield was obtained when the molar ratio was 2 AP:1 Ab. However, the tissue staining of the conjugates (anti-mouse—muscle, muscle actin; anti-rabbit—skin, S100) demonstrated that the best signal-to-noise ratio was seen with the 1:1 conjugate.

Example 17

Synthesis of Cross-linked AP

Alkaline phosphatase is a dimeric protein, and its stability can be increased by cross-linking the enzyme to help prevent dissociation of the dimer. Alkaline phosphatase was cross-linked using the following procedure. Alkaline phosphatase (Biozyme, San Diego, Calif.; 17.5 mg, 0.125 µmol) was exchanged into a different buffer from that in which it was received (0.1 M sodium phosphate, 0.1 M sodium chloride, 1.0 mM magnesium chloride, 0.1 mM zinc chloride, pH=7.5) and added to reconstituted, pre-oxidized, aldehyde-activated dextran (Avg. Molecular Wt. 40,000; Pierce Biotechnologies, Rockford, Ill.; 5 mg, 0.125 µmol) in the presence of sodium cyanoborohydride (1.6 mg, 25 µmol). The reaction mixture was then rotated for a period of one hour at room temperature. Excess aldehydes were quenched by ethanolamine (151 µl, 2.5 mmol) followed by addition of more sodium cyanoborohydride (157.1 mg, 2.5 mmol). The reaction mixture was rotated for an additional one hour. The cross-linked AP was isolated by size exclusion chromatography using an Akta Purifier (GE Biosciences, Uppsala, Sweden) equipped with a Superdex 200 GL 10/300 column (GE Biosciences, Uppsala, Sweden). The flow rate was 1 ml/min and the aqueous mobile phase was 0.1 M sodium phosphate, 0.1 M sodium chloride, 1.0 mM magnesium chloride, 0.1 mM zinc chloride, at pH=7.5. The number of amines remaining after the reaction was quantitated using a fluoraldehyde assay (Protein Assay Technical Handbook, Pierce Biotechnology, Rockford, Ill.), and on average 8-12 amines remained following cross-linking. The cross-linked AP was attached to MAL-dPEG$_{12}$-NHS ester (which reacted with the remaining amines) and was conjugated to an Fc-thiolated antibody as described in Example 4 to generate a conjugate including a cross-linked AP enzyme. Stability studies showed that cross-linking improved the stability of the conjugate in an avidin-containing diluent (Ventana Medical Systems, Inc, Tucson, Ariz.; P/N 95130). Specifically, at 45° C., the total loss of staining intensity on the $3^{rd}$ day for the conjugate with the cross-linked AP was 50%, whereas in the same diluent and at the temperature, a conjugate prepared with a non-crosslinked AP lost 95% of its staining intensity on the $1^{st}$ day.

Alternative methods for cross-linking AP to increase its stability are provided in Bieniarz et al., Bioconj. Chem., 9: 390-398, 1998, Bieniarz et al., Bioconj. Chem., 9: 399-402, 1998, and U.S. Pat. No. 5,789,219. These methods also can be used to cross-link alkaline phosphatase enzymes for use in a disclosed conjugate.

Example 18

Analytical SDS PAGE of Alkaline Phosphatase Conjugates

In this example, the Fc-specificity of the conjugation method of Example 4 is demonstrated by polyacrylamide gel electrophoresis under denaturing conditions. Six different preparations of the conjugate, 3 prepared with an anti-mouse IgG antibody and 3 prepared with an anti-rabbit IgG antibody were analyzed. Briefly, five to 20 µl of a 100-200 ng per µl solution of each conjugate was mixed with 4×LDS gel loading buffer (Invitrogen, Carlsbad, Calif.), and 2-Mercaptoethanol was added to a final concentration of 1 mM. The sample mixture was moderately heated at 48-50° C. for 5 minutes. This temperature was chosen to minimize dissociation of the covalent linkage between the enzyme and the antibody, while still permitting dissociating the light and heavy chains of the antibody portion of the conjugate by the 2-Mercaptoethanol. Each sample was then cooled and added to different wells of a polyacrylamide gel (either a 1.0-mm-thick, pre-formed NuPAGE™ 4-20% polyacrylamide Bis Tris gel or a NuPAGE™ 3-8% polyacrylamide Tris acetate gel from Invitrogen, Carlsbad, Calif.). The molecular weight standards used were pre-stained Multimark™ and Mark12 wide Range™ standards, both of which were purchased from Invitrogen (Carlsbad, Calif.). Electrophoresis was carried out at 70 mA for 60 to 90 minutes at room temperature using a Novex XCell II cassette system (Invitrogen, Carlsbad, Calif.). The running buffer was MES-SDS or Tris Acetate-SDS buffer, for the 3-8% and 4-20% gels, respectively. Gels were removed from the cassettes and washed twice in deionized water for 5 minutes in order to remove the SDS and buffer. The SDS-PAGE gels were then fixed in ethanol/water/acetic acid [40:50:10 (v:v:v)] for 1 hour at room temperature and stained with Coomassie Blue R-250 dissolved in methanol/water/acetic acid [50:40:10 (v:v:v), Sigma-Aldrich, St. Louis, Mo.]. The gels were stained for a minimum of 2 hours to a maximum of overnight by gentle rocking at room temperature. De-staining was carried out in the same manner as staining. The de-staining solution was identical to the staining solution minus the dye. Gels were dried using an Invitrogen gel drying kit (Invitrogen, Carlsbad, Calif.). Analysis of the gels clearly showed for each of the conjugates the presence of a band at a molecular weight corresponding to the light chain of the antibody. Also, for each conjugate, there was a substantial absence of bands corresponding to the molecular weight of the heavy chain and of alkaline phosphatase. Instead, a series of bands at higher molecular weights showed that the alkaline phosphatase was selectively bound to the heavy chain of the IgGs for each conjugate. Since the heavy chain of an immunoglobulin includes the Fc region, the results showed the Fc-site specific nature of the conjugation.

Example 19

Synthesis of an Fc-Specific Antibody-HRP Conjugate

In this example, preparation of an Fc-specific antibody conjugate including a PEG-based hydrazide thiol linker is described. Thiol-reactive maleimide groups were added to horseradish peroxidase as follows. To a 4 mL amber vial was added 7.8 mg (15.2 µmol, 100 eq.) of MAL-dPEG$_4$™NHS ester (Quanta Biodesign, Powell, Ohio), followed by horseradish peroxidase (HRP; Pierce Biotechnology, Rockford, Ill.; 0.25 ml, 25 mg/ml in 0.1 M Na$_3$PO$_4$, 0.15 M NaCl, pH=7.5). The vial was rotated in the dark at ambient temperature for 1 hour before being purified by size exclusion chromatography using an Akta Purifier equipped with a Superdex 200 column (GE Biosciences, Uppsala, Sweden) using an aqueous buffer solution (0.1 M Na$_3$PO$_4$, 0.15 M NaCl, pH=7.5). HRP containing fractions were pooled to give a solution of HRP-PEG$_4$-maleimide. The HRP concentration was determined from the $A_{280}$ of the solution ($\epsilon_{280}$=0.652 ml cm$^{-1}$ mg$^{-1}$) and the number of maleimides was quantitated through a modified Ellman's assay to be between 6 and 8 maleimides per enzyme.

The purified maleimido-horseradish peroxidase was combined with a purified thiolated antibody (according to Example 4, prepared using an MBH linker) in a 3:1 molar ratio and rotated for a period of 18 h. Size exclusion chromatography (Superdex 200; 0.1 M Na$_3$PO$_4$, 0.15 M NaCl, pH=7.5) gave the purified conjugate which was diluted to an $A_{280}$=0.0375 into Avidin Diluent with B5 Blocker (Ventana Medical Systems, Inc., Tucson, Ariz.) and analyzed on tissue. A comparison of staining of prostate specific antigen on prostate tissue using the HRP conjugate of this Example to an HRP conjugate prepared by DTT reduction of the immunoglobulin as described in U.S. Provisional Patent Application, No. 60/675,759 showed that the HRP conjugate of this Example exhibited slightly less background than the DTT-prepared HRP conjugate, but also exhibited slightly less staining intensity.

Example 20

Multifunctional Hydrazide Thiol Linkers Derived From Amino Acids

In some embodiments, multifunctional hydrazide thiol linkers that can be used in the disclosed method are prepared from amino acids and amino acid analogues according to schemes 4a, 4b, 4c and 4d above. In this example, synthetic routes to specific linkers are outlined in the following schemes. In each of specific schemes 17a, 17b, 17c and 17d, an amino acid or amino acid analog (Sigma-Aldrich, St. Louis, Mo.) is first reacted with N-Succinimidyl S-Acetylthioacetate (SATA; Pierce Biotechnology, Rockford, Ill.) in the presence of triethylamine (TEA). In scheme 17 a, the product of this first reaction is reacted with hydrazine to provide a multifunctional hydrazide thiol linker having one hydrazide group and two thiol groups. In Scheme 17b, carbodiimide-meditated coupling with DCC is used to form an NHS active ester with the carboxylic acid functionality of the product of the first reaction, followed by reaction with hydrazine to yield another multifunctional hydrazide thiol linker having one hydrazide group and two thiol groups. In Scheme 17c, as in 17b, NHS ester formation using the product of the first reaction is followed by reaction with hydrazine to yield a multifunctional hydrazide thiol linker having two hydrazide groups and one thiol group. In Scheme 17d, the reaction with hydrazine yields a multifunctional hydrazide thiol linker having one hydrazide group, one thiol group and one hydroxyl group.

Scheme 17a

Homocysteine derived

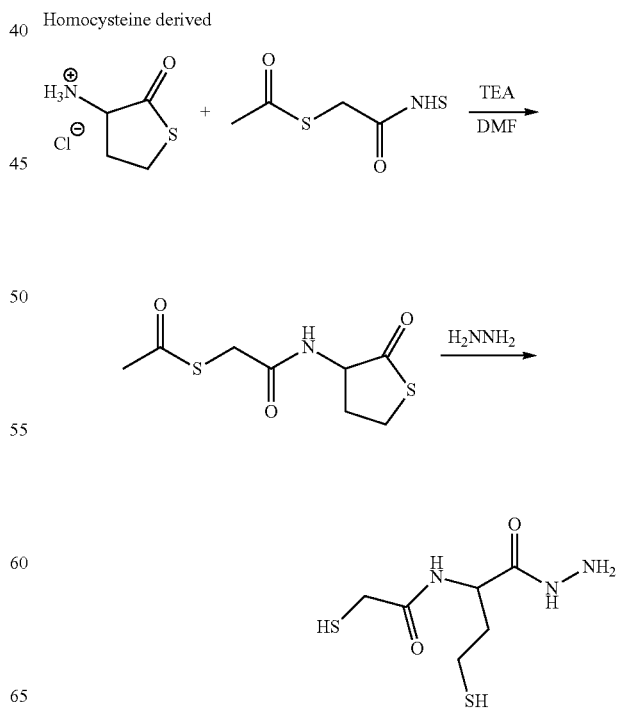

Scheme 17b

Lysine derived

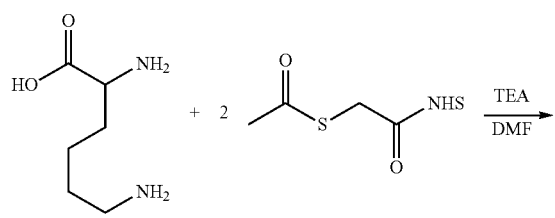

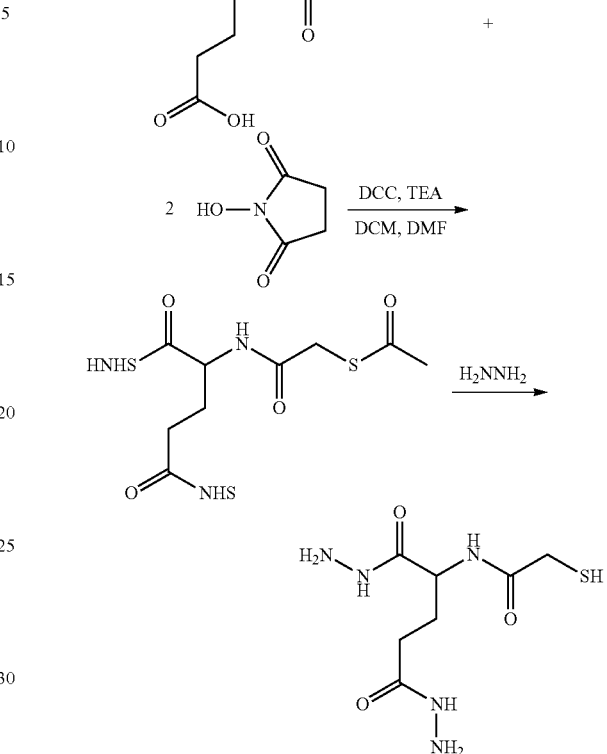

Scheme 17c

Glutamic Acid derived

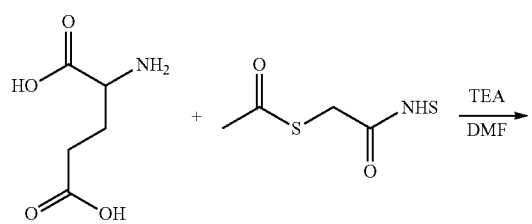

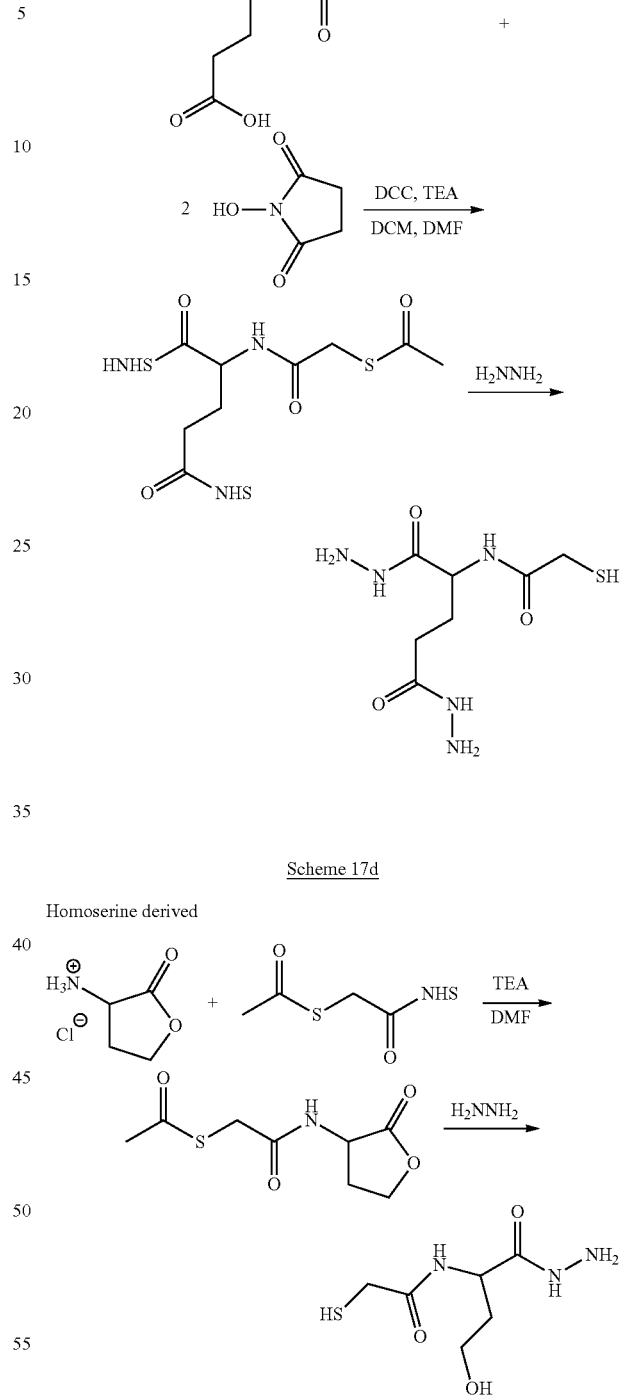

The products of Schemes 17a, 17b, 17c and 17d are, respectively, 2-mercaptoacetamido-mercaptobutyric acid hydrazide (MAMBH), N,N'-(6-hydrazinyl-6-oxohexane-1,5-diyl)bis(2-mercaptoacetamide) (BTAL), N-(1,5-dihydrazinyl-1,5-dioxopentan-2-yl)-2-mercaptoacetamide (TAGD) and N-(1-hydrazinyl-4-hydroxy-1-oxobutan-2-yl)-2-mercaptoacetamide.

In a particular embodiment, MAMBH is synthesized as follows. First S-Acetylthioacetamide homocysteine is prepared by preparing a solution of triethylamine (0.15 ml, 1.1 mmol) in acetonitrile (10 ml) to which was added homocysteine hydrochloride (150 mg, 1.0 mmol). The resulting slurry was stirred for 5 minutes before the addition of S-acetylthioacetate (250 mg, 1.1 mmol). The reaction was stirred for 16 h at ambient temperature and then concentrated in vacuo. Column chromatography (SiO$_2$, 9:1 CH$_2$Cl$_2$/Et$_2$O) resulted in the isolation of the product as a colorless powder. Yield: 174 mg (75%): $^1$H NMR (250 MHz, CDCl$_3$) δ 6.66 (bs, 1 H), 4.51-4.41 (p, J=6.7 Hz, 1 H), 3.63-3.50 (m, 2 H), 3.36-3.18 (m, 2 H), 2.88-2.80 (m, 1 H), 2.38 (s, 3 H), 2.01-1.88 (m, 1 H); $^{13}$C NMR (62.9 MHz, CDCl$_3$) δ 204.37, 195.38, 168.59, 59.51, 32.74, 31.43, 30.18, 27.43; ESI-HRMS m/z 256.00693 (M+Na$^+$, C$_8$H$_{11}$NNaO$_3$S$_2$ calcd 256.00780). 2-Mercaptoacetamido-mercaptobutyric acid hydrazide (MAMBH) is then prepared by adding the S-acetylthioacetamide homocysteine (300 mg, 1.3 mmol) to hydrazine monohydrate (10 ml). The resulting slurry was stirred for 16 h at ambient temperature at which time the solution becomes homogeneous. The hydrazine was removed in vacuo and the crude product was purified by reverse-phase flash chromatography (15% C$_8$ SiO$_2$, 160:39:1 H$_2$O/MeOH/AcOH) to give the desired compound as a colorless oil. Yield: 207 mg (72%): $^1$H NMR (250 MHz, CD$_3$OD) δ 4.52-4.46 (m, 1 H), 3.23-3.21 (m, 2 H), 2.59-2.52 (m, 2 H), 2.10-2.01 (m, 2 H); $^{13}$C NMR (62.9 MHz, CD$_3$OD) δ 172.82, 172.43, 52.49, 37.72, 21.42, 20.49; ESI-HRMS m/z 246.03251 (M+Na$^+$, C$_6$H$_{13}$N$_3$NaO$_2$S$_2$ calcd 246.03469).

Substitution of 6-Acetylthiohexanoic acid NHS ester for SATA in schemes 17a, 17b and 17c yields the corresponding compounds TMBH, BTHL and THGD that are shown below. 6-Acetylthiohexanoic acid NHS ester has the following structure 6-Acetylthiohexanoic acid NHS ester can be prepared from by carbodiimide mediated coupling of 6-Acetylthiohexanoic acid with N-Hydroxysuccinimide.

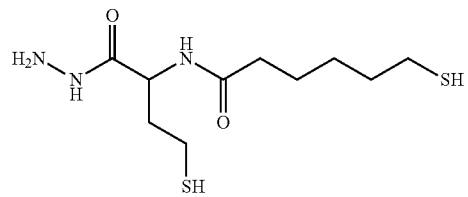

Thiohexanamidomercaptobutyric acid hydrazide (THMBH)

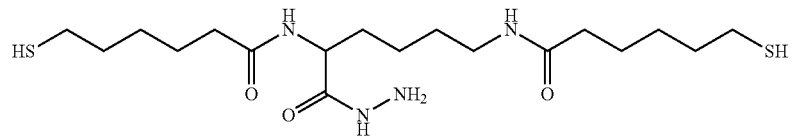

Bisthiohexanamidohydrazidolysine (BTHL)

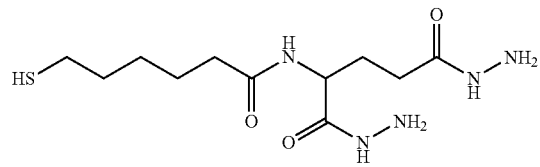

Thiohexamidoglutamic acid dihydrazide (THGD)

6-Acetylthiohexanoic acid NHS ester has the following structure:

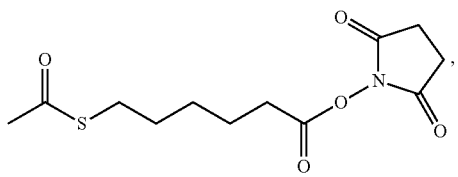 [SMILES: CC(=O)SCCCCCC(=O)ON1C(=O)CCC1=O]

and is prepared by carbodiimide mediated coupling of 6-Acetylthiohexanoic acid with N-Hydroxysuccinimide (both available from Sigma-Aldrich, St. Louis, Mo.).

One of ordinary skill in the art also will recognize that PEG-based S-acetyl-thiocarboxylic acid derivatives can be substituted for SATA in the schemes above to provide multifunctional PEG-based linkers that be used in the disclosed method of conjugation. For example, PEG-based multifunctional hydrazide thiol linkers can be made by substituting a molecule of the following formula for SATA in schemes 17 a-d above:

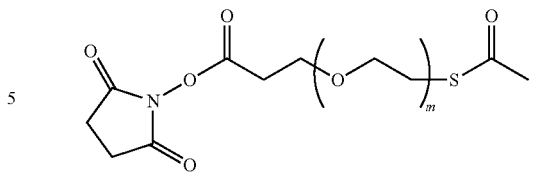

wherein m=2 to 50. Compounds of this formula are commercially available from Quanta Biodesign (Powell, Ohio), or can be prepared from corresponding carboxylic acids.

Example 21

Multifunctional PEG-based Hydrazide Thiol Linkers

In some embodiments, multifunctional PEG-based hydrazide thiol linkers that can be used in the disclosed method are prepared according to schemes 5a, 5b and 5c above. In this example, synthetic routes to specific linkers are outlined in the following schemes 18a, 18b and 18c. Specific protocols for the reactions also are presented. Unless otherwise stated, reagents and solvents are conventional and can be obtained, for example, from Sigma-Aldrich (St. Louis, Mo.).

Scheme 18a

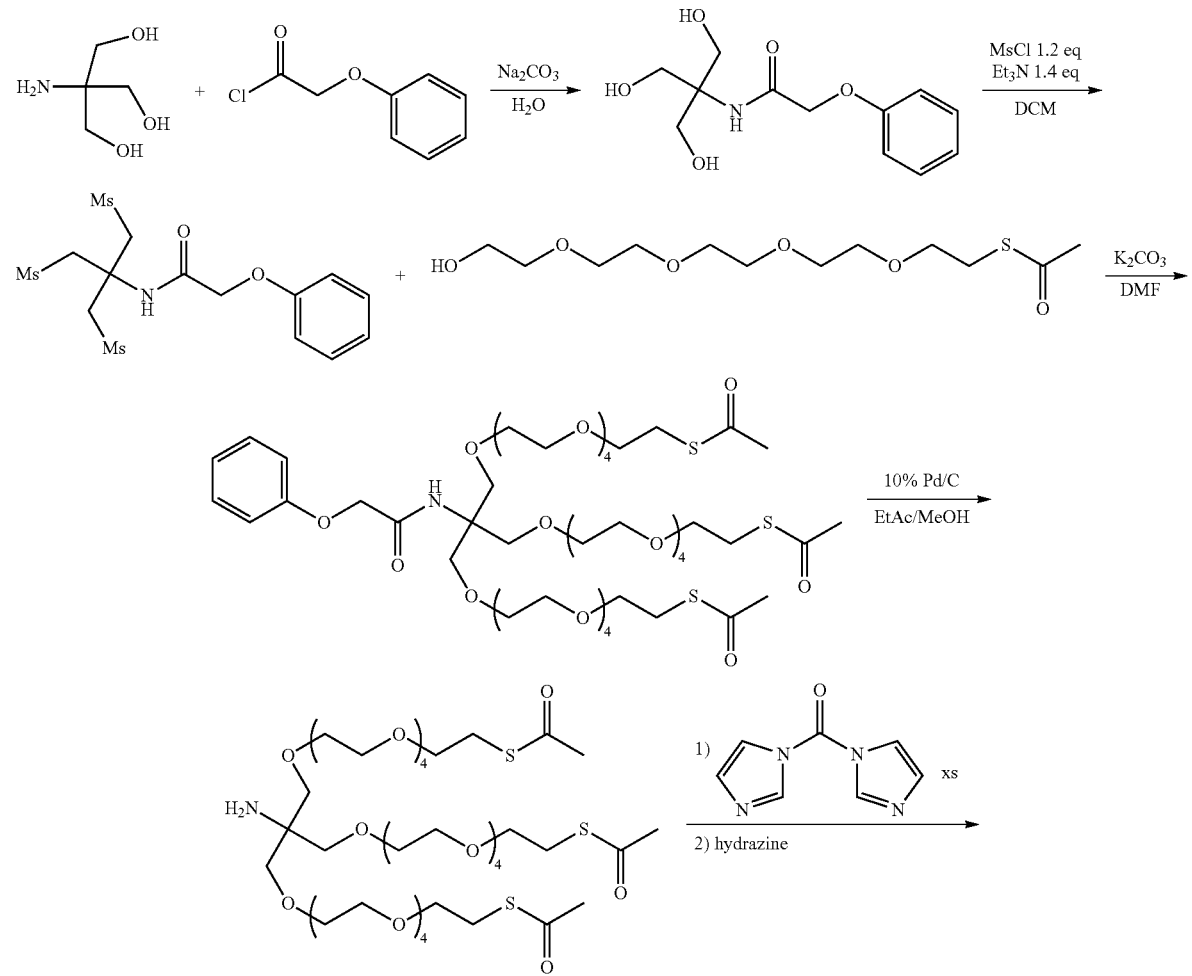

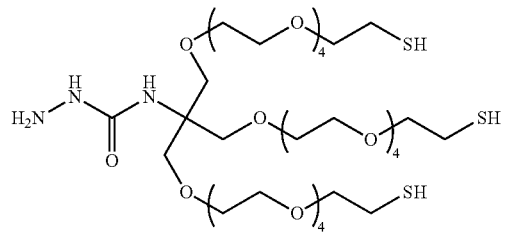

According to Scheme 18a, to a solution of 5.0 grams of Tris in 10 ml water is added sodium carbonate (1.3 eq) followed by phenoxy acetylchloride (1.2 eq), and the reaction is allowed to stir on ice under nitrogen for 16 hours. The precipitated amino protected product is then washed three times with water and dried under vacuum. The pure compound resulting from this first reaction is obtained by chromatography on a C18 silica based column eluted with acetonitrile/H2O, 5-100% acetonitrile over 30 minutes. Mesylate groups are then introduced by treating with triethylamine (4.0 eq) and methane sulfonyl chloride (5.0 eq) in DMF. The DMF is removed under vacuum, the residue taken in dry DCM and the salts removed by filtration. Removal of the DCM under vacuum gives the crude mesylate 2 which is used without further purification. To a solution of the mesylate (0.3 eq) in dry DMF is added HO-dPEG$_{4^{TM}\text{-}SATA}$ (1.0 eq; Quanta Biodesign, Powell, Ohio) and K$_2$CO$_3$ (1.5 eq) and the reaction allowed to stir under nitrogen for 16 hours. The DMF is removed under vacuum, the residue taken in dry DCM and salts are removed by filtration. Removal of the DCM under vacuum followed by silica gel chromatography gives the pegylated intermediate. The Pac protecting group is then removed by treating with Pd/C in a mixture of EtAc/MeOH. The semicarbizide is then elaborated by treating the resulting intermediate first with carbonyl diimidizole (10 eq) followed by hydrazine (100 eq).

Scheme 18b

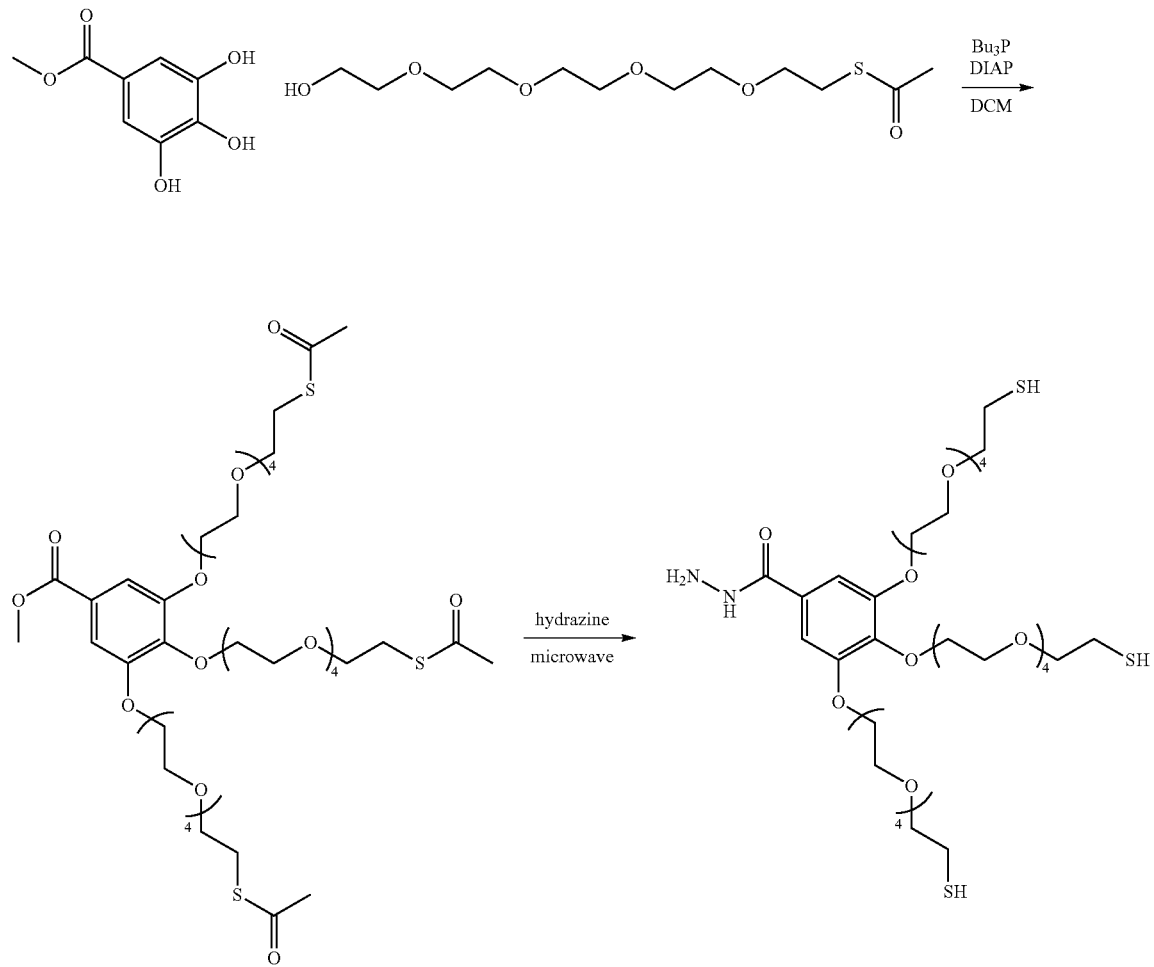

According to Scheme 18b, to a solution of alcohol (HO-PEG4-SATA, Quanta Biodesign, Powell, Ohio, 1.3 eq) in DCM is added 1.5 eq of diazo-diisopropyldicarboxylate followed by 1.8 eq of tributyl phosphine, and the reaction is stirred under dry nitrogen for 30 minutes. To the resulting suspension is then added 1.0 eq of the phenol in DCM and the reaction allowed to stir under dry nitrogen for 16 hrs. The phenol ether obtained after silica gel chromatography is then taken in neat hydrazine and the solution is microwaved to give the multi functional PEG-based hydrazide thiol linker.

Scheme 18c

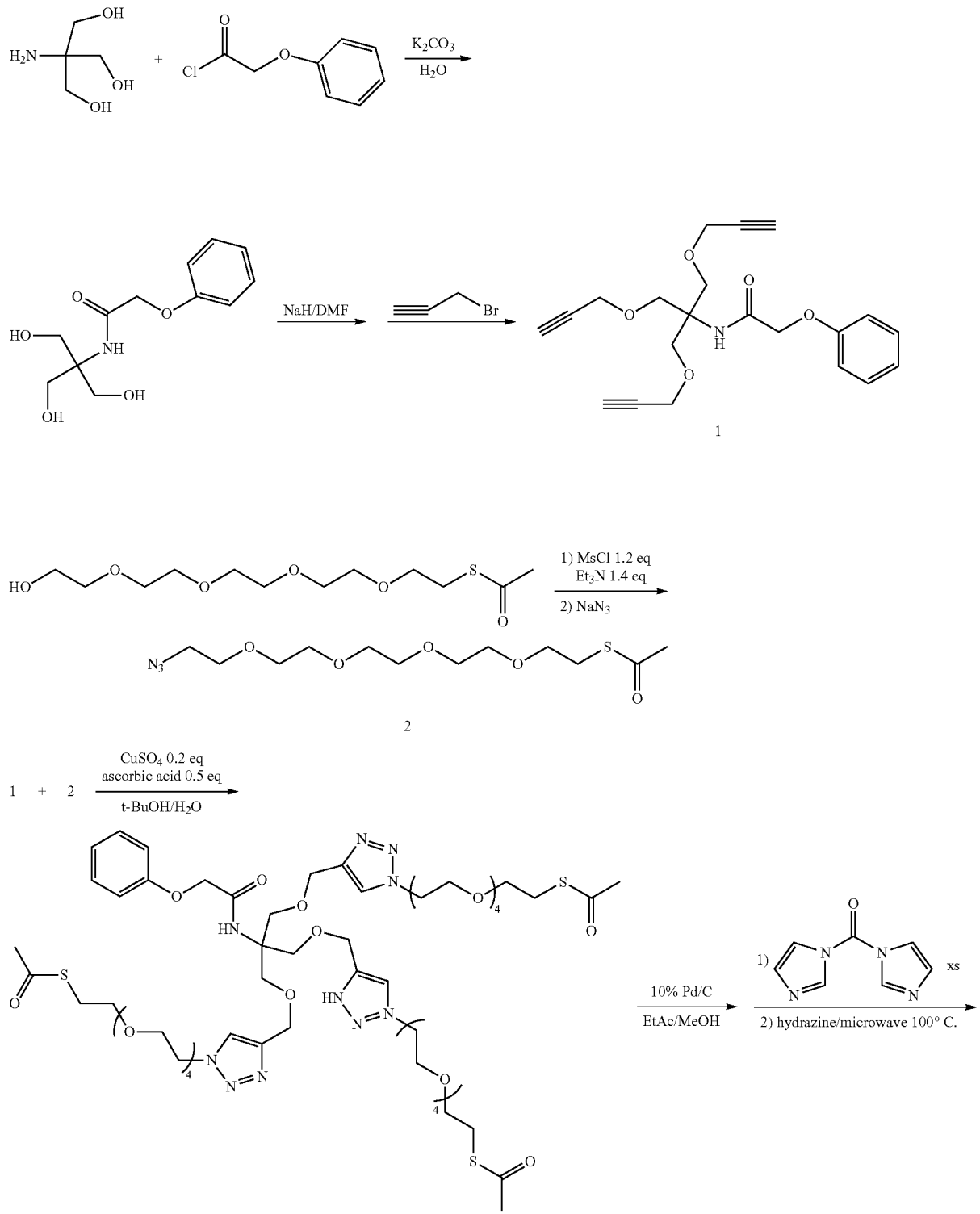

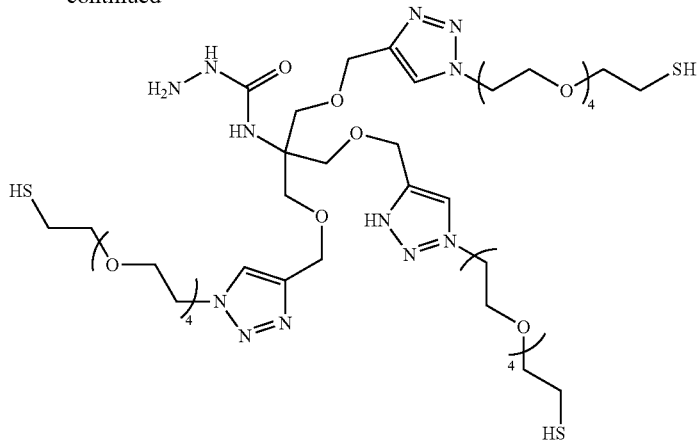

According to Scheme 18c, to a solution of 5.0 grams of Tris in 10 ml water is added potassium carbonate (1.3 eq) followed by phenoxy acetylchloride (1.2 eq), and the reaction is allowed to stir on ice under nitrogen for 16 hours. The precipitated amino protected product is then washed three times with water and dried under vacuum. The alkyne groups are then introduced by treating with sodium hydride (3.0 eq) and propargyl bromide (10 eq) in DMF to give the alkyne intermediate 1 after silica gel chromatography. To a solution of HO-PEG$_4$-SATA (Quanta Biodesign, Powell, Ohio) in DCM is added methane sulfonyl chloride (1.2 eq) followed by triethyl amine (1.4 eq), and the reaction allowed to stir on ice under nitrogen for 16 hours. The triethyl amine salt is then removed by filtration and the mesylate product dried under vacuum. To a solution of the mesylated alcohol in DCM is added sodium azide (1.2 eq), and the reaction allowed to stir under nitrogen for 16 hours to afford the azide intermediate 2 after silica gel chromatography. To a 1:1 solution of t-butanol/water containing copper sulfate (0.2 eq) and sodium ascorbate (0.5 eq) is added one equivalent each of the intermediate alkyne 1 and the intermediate azide 2. The reaction then stirred under nitrogen for sixteen hours to afford the intermediate with the protected nitrogen after silica gel chromatography. The nitrogen protecting group is then removed by treating with 10% Pd/C in a 1:1 mixture of ethyl acetate and methanol and the free amine then obtained by an acid-base work up. To a solution of the free amine in DCM is added carbonyl diimidizole (10 eq), and the reaction stirred under nitrogen for four hours. The reaction is then concentrated under vacuum and the residue taken into neat hydrazine. The solution is then microwave at 100° C. for 1 hour to give the multifunctional PEG-based hydrazide thiol linker.

It will be readily apparent to one skilled in the art that the PEG-based molecules can be replaced with other SATA alcohols in these schemes to provide additional multifunctional PEG-based hydrazide thiol linkers, and that PEG SATA alcohols of differing lengths can be substituted as well.

Example 22

Synthesis of a Polyacrylamide Hydrazide Thiol Linker

In this example, a polymeric multivalent hydrazide thiol linker is provided, which linker can be prepared according to Scheme 19 below.

Scheme 19

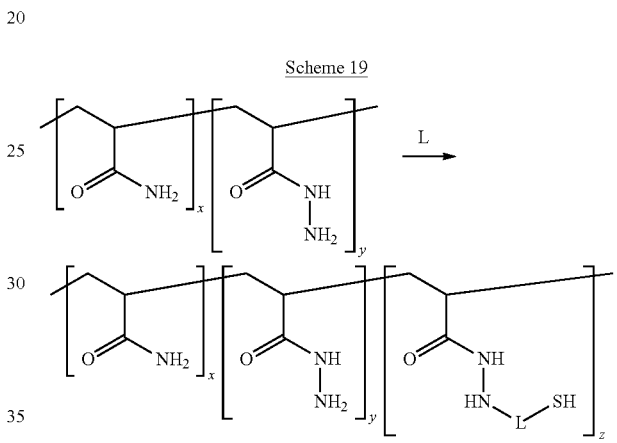

In Scheme 19, x can be, for example, 100-500 and y can be, for example, 10-50. L represents a thiolating reagent used to convert a portion of the hydrazide groups to thiol groups. Polyacrylamide hydrazide (PAH) can be synthesized by the method provided in published U.S. Patent Application No. 20050158770. Briefly, in a 100 mL round-bottom flask fitted with a condenser, 20 mL polyacrylamide (1 mmol, 50% wt in water, Sigma-Aldrich, Milwaukee, Wis.) is mixed with 10 mL distilled (DI) water and 20 mL hydrazine monohydrate (420 mmol, Sigma-Aldrich, Milwaukee, Wis.). The reaction is microwaved for 60 min. After cooling to room temperature, the reaction is precipitated with an equal volume of methanol, centrifuged and decanted. The residue is taken up in 50 mL DI water and the precipitation repeated for a total of three times. The final residue is dissolved in DI water and lyophilized to give a fine, white hygroscopic powder. In an appropriate solvent, the resulting PAH is reacted with a thiolating agent, such as a thiol-dPEG-NHS ester (Quanta Biodesign, Powell, Ohio) or Traut's reagent, to thiolate a portion (for example, approximately 50-75%) of available hydrazides (z=5 to 40) and provide a polymeric multifunctional hydrazide thiol linker that can be used in the disclosed method. Additional thiolating reagents can be found, for example, in Hermanson, "Bioconjugate Techniques," Academic Press, San Diego, 1996, ISBN 0-12-342336-8, which is incorporated by reference herein.

It is possible to use/prepare the polyacrylamide hydrazide thiol linker in one of two ways, either synthesize it first and use the disclosed conjugation method, or first react PAH with one molecule, thiolate the PAH, and then react the now thiolated first molecule with a second molecule.

Although the principles of the present invention have been described with reference to several illustrative embodiments, it should be apparent to those of ordinary skill in the art that the details of the embodiments may be modified without departing from such principles. For example, although the detailed description has focused on antibody-enzyme conjugates, the linkers and methods can be used to prepare any type of conjugate including conjugates of antibodies and other detectable labels such as nanoparticles (for example, metal and semiconductor nanoparticles such as gold nanoparticles and quantum dots, respectively), fluorescent molecules, fluorogenic molecules, colored molecules, colorogenic molecules, and paramagnetic constructs (such as chelates of paramagnetic ions). Conjugates of antibodies for directed therapies (for example, conjugates of antibodies with drug molecules, toxins and radioactive constructs such as chelates of radioactive metal ions) also are contemplated. Although, specific examples provided show the use of hydrazide thiol linkers having hydrazide and carbohydrazide groups, any "hydrazide group" can be substituted for the hydrazide or carbohydrazide groups shown in both the disclosed method and the disclosed conjugate. Furthermore, it should be understood that while one or more of a single hydrazide thiol linker can be used to form a conjugate, it is also possible to use multiple different hydrazide thiol linkers to form a conjugate. The disclosed conjugates can be used in any type of assay where a specific binding molecule attached to a detectable label can be used, for example, in any type of immunoassay in addition to the illustrated immunohistochemical assays, or in any type of in situ hybridization assay. Detection protocols can be performed manually or in an automated fashion. Furthermore, the disclosed linkers also can be used to modify surfaces for binding molecules to a substrate, and such surface modification reactions can be performed using the disclosed method. The present invention includes all modifications, variations, and equivalents thereof as fall within the scope and spirit of the following claims.

We claim:

1. A kit, comprising:
a conjugate, comprising
   an antibody,
   a detectable label comprising an enzyme including about 17-25 maleimide groups introduced into the enzyme by NHS-PEG-maleimide linkers, each linker being covalently bonded to an amino group of the enzyme, and
   a plurality of hydrazide thiol linkers, each hydrazide thiol linker comprising one or more linking atoms positioned between a hydrazide group and a thiol group, wherein the hydrazide thiol linker is selected from mercaptobutyric acid hydrazide (MBH), mercaptobutyric acid carbohydrazide (MBCH), mercaptoacetamido-mercaptobutyric acid hydrazide (MAMBH), thiohexanamidomercaptobutyric acid hydrazide (THMBH), N,N'-(6-hydrazinyl-6-oxohexane-1,5-diyl)bis(2-mercaptoacetamide) (BTAL), bisthiohexanamidohydrazidolysine (BTHL), N-(1,5-dihydrazinyl-1,5-dioxopentan-2-yl)2-mercaptoacetamide (TAGD), thiohexamidoglutamic acid dihydrazide (THGD), a PEG-based hydrazide-thiol linker, a multifunctional hydrazide thiol linker, a PEG-based multifunctional hydrazide thiol linker, a polyacrylamide hydrazide thiol linker, and combinations thereof, the hydrazide group of each hydrazide thiol linker being covalently bonded to an oxidized glycosylated Fc portion of the antibody and the thiol group of one of the hydrazide thiol linkers being covalently bonded to the detectable label via one of the maleimide groups.

2. The kit of claim 1, wherein the hydrazide thiol linker comprises a PEG-based hydrazide thiol linker.

3. The kit of claim 2, wherein the PEG-based hydrazide thiol linker comprises a mercapto-dPEG-hydrazide linker.

4. The kit of claim 1, wherein the hydrazide thiol linker comprises MBH or MBCH.

5. The kit of claim 1, wherein the enzyme is alkaline phosphatase or horseradish peroxidase.

6. The kit of claim 5, wherein the enzyme is alkaline phosphatase.

7. The kit of claim 6, wherein the alkaline phosphatase comprises cross-linked alkaline phosphatase.

8. The kit of claim 1, wherein the antibody comprises an anti-hapten antibody.

9. The kit of claim 1, wherein the antibody comprises an anti-antibody antibody.

10. A method for detecting a molecule of interest in a cell or tissue sample, comprising: contacting the cell or the tissue sample with a primary antibody specifically recognizing the molecule of interest in the cell or the tissue sample to provide the cell or the tissue sample bound with the primary antibody
   contacting the cell or tissue sample with a conjugate comprising
      an antibody capable of specifically recognizing the primary antibody,
      a detectable label comprising an enzyme including about 17-25 maleimide groups introduced into the enzyme by NHS-PEG-maleimide linkers, each linker being covalently bonded to an amino group of the enzyme, and
      a plurality of hydrazide thiol linkers, each hydrazide thiol linker comprising one or more linking atoms positioned between a hydrazide group and a thiol group, wherein the hydrazide thiol linker is selected from mercaptobutyric acid hydrazide (MBH), mercaptobutyric acid carbohydrazide (MBCH), mercaptoacetamido-mercaptobutyric acid hydrazide (MAMBH), thiohexanamidomercaptobutyric acid hydrazide (THMBH), N,N'-(6-hydrazinyl-6-oxohexane-1,5-diyl)bis(2-mercaptoacetamide) (BTAL), bisthiohexanamidohydrazidolysine (BTHL), N-(1,5-dihydrazinyl-1,5-dioxopentan-2-yl)2-mercaptoacetamide (TAGD), thiohexamidoglutamic acid dihydrazide (THGD), a PEG-based hydrazide-thiol linker, a multifunctional hydrazide thiol linker, a PEG-based multifunctional hydrazide thiol linker, a polyacrylamide hydrazide thiol linker, and combinations thereof, the hydrazide group of each hydrazide thiol linker being covalently bonded to an oxidized glycosylated Fc portion of the antibody and the thiol group of one of the hydrazide thiol linkers being covalently bonded to one of the maleimide groups on the enzyme; and
   detecting a signal generated by the conjugate that are bound to the primary antibody indicating the presence of the molecule of interest in the cell or tissue sample.

11. The method of claim 10, wherein the hydrazide thiol linker comprises a PEG-based hydrazide thiol linker.

12. The method of claim 11, wherein the PEG-based hydrazide thiol linker comprises a mercapto-dPEG-hydrazide linker.

13. The method of claim 10, wherein the hydrazide thiol linker comprises MBH or MBCH.

14. The method of claim 10, wherein the enzyme is alkaline phosphatase or horseradish peroxidase.

15. The method of claim 14, wherein the enzyme is alkaline phosphatase.

16. The method of claim 15, wherein the alkaline phosphatase comprises cross-linked alkaline phosphatase.

* * * * *